United States Patent
Bardy et al.

(10) Patent No.: US 10,433,751 B2
(45) Date of Patent: Oct. 8, 2019

(54) SYSTEM AND METHOD FOR FACILITATING A CARDIAC RHYTHM DISORDER DIAGNOSIS BASED ON SUBCUTANEOUS CARDIAC MONITORING DATA

(71) Applicant: Bardy Diagnostics, Inc., Seattle, WA (US)

(72) Inventors: Gust H. Bardy, Carnation, WA (US); Ezra M. Dreisbach, Vashon, WA (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

(21) Appl. No.: 16/178,463

(22) Filed: Nov. 1, 2018

(65) Prior Publication Data
US 2019/0069794 A1 Mar. 7, 2019

Related U.S. Application Data

(63) Continuation-in-part of application No. 16/102,608, filed on Aug. 13, 2018, and a continuation-in-part of
(Continued)

(51) Int. Cl.
*A61B 5/0456* (2006.01)
*A61B 5/044* (2006.01)
(Continued)

(52) U.S. Cl.
CPC .......... *A61B 5/0456* (2013.01); *A61B 5/0245* (2013.01); *A61B 5/02405* (2013.01);
(Continued)

(58) Field of Classification Search
CPC . A61B 5/0452; A61B 5/02405; A61B 5/0245; A61B 5/04085; A61B 5/04087;
(Continued)

(56) References Cited

U.S. PATENT DOCUMENTS

| 3,215,136 A | 11/1965 | Holter et al. |
| 3,569,852 A | 3/1971 | Berkovits |

(Continued)

FOREIGN PATENT DOCUMENTS

| DE | 19955211 | 5/2001 |
| EP | 1859833 | 11/2007 |

(Continued)

OTHER PUBLICATIONS 15 of The Hottest Wearable Gadgets, URL <http://thehottestgadgets.com/2008/09/the-15-hottest-wearable-gadgets-001253> (Web page cached on Sep. 27, 2008).

(Continued)

*Primary Examiner* — Paula J Stice
(74) *Attorney, Agent, or Firm* — Patrick J. S. Inouye; Leonid Kisselev

(57) ABSTRACT

A system and method for facilitating a cardiac rhythm disorder diagnosis based on subcutaneous cardiac monitoring data with the aid of a digital computer are provided. Cutaneous action potentials of a patient are recorded as electrocardiogram (EGC) data over a set time period using a subcutaneous insertable cardiac monitor. A set of R-wave peaks is identified within the ECG data and an R-R interval plot is constructed. A difference between recording times of successive pairs of the R-wave peaks in the set is determined. A heart rate associated with each difference is also determined. The pairs of the R-wave peaks and associated heart rate are plotted as the R-R interval plot. A diagnosis of cardiac disorder is facilitated based on patterns of the plotted pairs of the R-wave peaks and the associated heart rates in the R-R interval plot.

20 Claims, 13 Drawing Sheets

Related U.S. Application Data application No. 15/832,385, filed on Dec. 5, 2017, and a continuation of application No. 15/231,752, filed on Aug. 8, 2016, now Pat. No. 10,045,709, which is a continuation of application No. 15/066,883, filed on Mar. 10, 2016, now Pat. No. 9,408,551, which is a continuation-in-part of application No. 14/997,416, filed on Jan. 15, 2016, now Pat. No. 9,345,414, which is a continuation-in-part of application No. 14/614,265, filed on Feb. 4, 2015, now Pat. No. 9,408,545, which is a continuation-in-part of application No. 14/488,230, filed on Sep. 16, 2014, now Pat. No. 9,700,227, which is a continuation-in-part of application No. 14/080,725, filed on Nov. 14, 2013, now Pat. No. 9,730,593.

(60) Provisional application No. 62/132,497, filed on Mar. 12, 2015, provisional application No. 61/882,403, filed on Sep. 25, 2013.

(51) Int. Cl.
*A61B 5/0432* (2006.01)
*A61B 5/00* (2006.01)
*A61B 5/0408* (2006.01)
*A61B 5/0452* (2006.01)
*A61B 5/0245* (2006.01)
*A61B 5/024* (2006.01)
*A61B 5/042* (2006.01)
*A61B 5/04* (2006.01)
*A61B 5/046* (2006.01)
*A61B 5/0468* (2006.01)
*A61B 5/0464* (2006.01)
*A61B 5/0205* (2006.01)

(52) U.S. Cl.
CPC ............ *A61B 5/044* (2013.01); *A61B 5/0422* (2013.01); *A61B 5/0432* (2013.01); *A61B 5/04085* (2013.01); *A61B 5/04087* (2013.01); *A61B 5/04525* (2013.01); *A61B 5/686* (2013.01); *A61B 5/6823* (2013.01); *A61B 5/7203* (2013.01); *A61B 5/0205* (2013.01); *A61B 5/02055* (2013.01); *A61B 5/046* (2013.01); *A61B 5/04011* (2013.01); *A61B 5/04017* (2013.01); *A61B 5/0464* (2013.01); *A61B 5/0468* (2013.01); *A61B 5/742* (2013.01); *A61B 2560/0468* (2013.01); *A61B 2562/162* (2013.01)

(58) Field of Classification Search
CPC ..... A61B 5/0422; A61B 5/0432; A61B 5/044; A61B 5/04525; A61B 5/6823; A61B 5/686
See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bomn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |

(56) References Cited

U.S. PATENT DOCUMENTS

| | | |
|---|---|---|
| 6,427,083 B1 | 7/2002 | Owen et al. |
| 6,427,085 B1 | 7/2002 | Boon et al. |
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bomzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Massif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |

(56) References Cited

U.S. PATENT DOCUMENTS

| | | |
|---|---|---|
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0054737 A1 | 3/2006 | Richardson |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0312522 A1 | 12/2008 | Rowlandson et al. |
| 2009/0012412 A1 | 1/2009 | Wesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1* | 10/2009 | van Dam ............ A61B 5/04525 600/509 |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |

(56) References Cited

U.S. PATENT DOCUMENTS

| | | |
|---|---|---|
| 2012/0089412 A1 | 4/2012 | Bishay et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shustemian |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2017/0112399 A1 | 4/2017 | Brisben et al. |
| 2017/0156592 A1 | 6/2017 | Fu |
| 2017/0281032 A1 | 10/2017 | Weinberg et al. |
| 2017/0366921 A1 | 12/2017 | Pflugh et al. |
| 2018/0078771 A1 | 3/2018 | Koop et al. |
| 2019/0021671 A1 | 1/2019 | Kumar et al. |
| 2019/0059763 A1 | 2/2019 | Shakur et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 6/2010 |
| WO | 2011047207 | 4/2011 |
| WO | 2012140559 | 10/2012 |
| WO | 2012146957 | 11/2012 |
| WO | 2017072250 | 5/2017 |

OTHER PUBLICATIONS

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs A Band-Aid, "Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/us/en_us/c/nikeplus-fuelband> (Web page cached on Jan. 11, 2013.).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> (Sep. 17, 2013).

Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).

(56) References Cited

OTHER PUBLICATIONS

Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2011).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2011).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).
ADINSTRUMENTS:ECG Analysis Module for LabChart & PowerLab, 2008.
BIOPAC Systems, Inc. #AS148-Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under The Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
Pranav Rajpurkar et al. "Cardiologist-Level Arrhythmia Detection with Convolutional Neural Networks,"ARXIV. ORG, Cornell University Library, 201 Olin Library Cornell University Ithaca, NY 14853, Jul. 6, 2017 (Jul. 6, 2017), XP080774895.
Bourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.
Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.

\* cited by examiner (a)

(b)

SYSTEM AND METHOD FOR FACILITATING A CARDIAC RHYTHM DISORDER DIAGNOSIS BASED ON SUBCUTANEOUS CARDIAC MONITORING DATA

CROSS-REFERENCE TO RELATED APPLICATION

This non-provisional patent application is a continuation-in-part of U.S. patent application Ser. No. 16/102,608, filed Aug. 13, 2018, pending, which is a continuation of U.S. Pat. No. 10,045,709, issued Aug. 14, 2018; which is a continuation of U.S. Pat. No. 9,408,551, issued Aug. 9, 2016; which is a continuation-in-part of U.S. Pat. No. 9,345,414, issued May 24, 2016; which is a continuation-in-part of U.S. Pat. No. 9,408,545, issued Aug. 9, 2016; which is a continuation-in-part of U.S. Pat. No. 9,700,227, issued Jul. 11, 2017; which is a continuation-in-part of U.S. Pat. No. 9,730,593, issued Aug. 15, 2017; and further claims priority under 35 U.S.C. § 119(e) to U.S. Provisional Patent Application Ser. No. 62/132,497, filed Mar. 12, 2015, and U.S. Provisional Patent Application Ser. No. 61/882,403, filed Sep. 25, 2013, the disclosures of which are incorporated by reference; this present non-provisional patent application is also a continuation-in-part of U.S. patent application Ser. No. 15/832,385, filed Dec. 5, 2017, pending, the disclosure of which is incorporated by reference.

FIELD

This application relates in general to electrocardiographic monitoring and, in particular, to a system and method for facilitating diagnosis of cardiac rhythm disorders based on subcutaneous cardiac monitoring data.

BACKGROUND

An electrocardiogram (ECG) allows physicians to diagnose cardiac function by visually tracing the cutaneous electrical signals (action potentials) that are generated by the propagation of the transmembrane ionic currents that trigger the depolarization of cardiac fibers. An ECG trace contains alphabetically-labeled waveform deflections that represent distinct features within the cyclic cardiac activation sequence. The P-wave represents atrial depolarization, which causes atrial contraction. The QRS-complex represents ventricular depolarization. The T-wave represents ventricular repolarization.

The R-wave is often used as an abbreviation for the QRS-complex. An R-R interval spans the period between successive R-waves and, in a normal heart, is 600 milliseconds (ms) to one second long, which respectively correspond to 100 to 60 beats per minute (bpm). The R-wave is the largest waveform generated during normal conduction and represents the cardiac electrical stimuli passing through the ventricular walls. R-R intervals provide information that allows a physician to understand at a glance the context of cardiac rhythms both before and after a suspected rhythm abnormality and can be of confirmational and collaborative value in cardiac arrhythmia diagnosis and treatment.

Conventionally, the potential of R-R interval context has not been fully realized, partly due to the difficulty of presentation in a concise and effective manner to physicians. For instance, routine ECGs are typically displayed at an effective paper speed of 25 millimeters (mm) per second. A lower speed is not recommended because ECG graph resolution degrades at lower speeds and diagnostically-relevant features may be lost. Conversely, a half-hour ECG recording, progressing at 25 mm/s, results in 45 meters of ECG waveforms that, in printed form, is cumbersome and, in electronic display form, will require significant back and forth toggling between pages of waveforms, as well as presenting voluminous data transfer and data storage concerns. As a result, ECGs are less than ideal tools for diagnosing cardiac arrhythmia patterns that only become apparent over an extended time frame, such as 30 minutes or longer.

R-R intervals have also been visualized in Poincare plots, which graph RR(n) on the x-axis and RR(n+1) on the y-axis. However, a Poincare plot fails to preserve the correlation between an R-R interval and the R-R interval's time of occurrence and the linearity of time and associated contextual information, before and after a specific cardiac rhythm, are lost. In addition, significant changes in heart rate, particularly spikes in heart rate, such as due to sinus rhythm transitions to atrial flutter or atrial fibrillation, may be masked or distorted in a Poincare plot if the change occurs over non-successive heartbeats, rather than over two adjacent heartbeats, which undermines reliance on Poincare plots as dependable cardiac arrhythmia diagnostic tools. Further, Poincare plots cannot provide context and immediate temporal reference to the actual ECG, regardless of paper speed. Events both prior to and after a specific ECG rhythm can provide key clinical information disclosed in the R-R interval plot that may change patient management above and beyond the specific rhythm being diagnosed.

Further, in addition to the information that a physician can understand from an R-R interval plot, the P-wave is a critical component of arrhythmia monitoring and diagnosis performed every day hundreds of thousands of times across the United States. Without a knowledge of the relationship of these two basic symbols, heart rhythm disorders cannot be reliably diagnosed. Visualizing both the P-wave and the R-wave allow for the specific identification of a variety of atrial tachyarrhythmias (also known as supraventricular tachyarrhythmias, or SVTs), ventricular tachyarrhythmias (VTs), and bradycardias related to sinus node and atrioventricular (AV) node dysfunction. These categories are well understood by cardiologists but only accurately diagnosable if the P-wave and the R-wave are visualized and their relationship and behavior are clear. Visualization of the R-wave is usually readily achievable, as the R-wave is a high voltage, high frequency signal easily recorded from the skin's surface. However, as the ECG bipole spacing and electrode surface area decreases, even the R-wave can be a challenge to visualize. To make matters of rhythm identification more complicated, surface P-waves can be much more difficult to visualize from the surface because of their much lower voltage and signal frequency content. P-wave visualization becomes exacerbated further when the recording bipole inter-electrode spacing decreases.

Cardiac rhythm disorders may present with lightheadedness, fainting, chest pain, hypoxia, syncope, palpitations, and congestive heart failure (CHF), yet rhythm disorders are often sporadic in occurrence and may not show up in-clinic during a conventional 12-second ECG. Continuous ECG monitoring with P-wave-centric action potential acquisition over an extended period is more apt to capture sporadic cardiac events. However, recording sufficient ECG and related physiological data over an extended period remains a significant challenge. For instance, maintaining continual contact between ECG electrodes of conventional ambulatory dermal ECG monitors and the skin after a day or two of ambulatory ECG monitoring has been a problem. Time, dirt, moisture, and other environmental contaminants, as well as perspiration, skin oil, and dead skin cells from the patient's body, can get between an ECG electrode's non-conductive adhesive and the skin's surface. These factors adversely affect electrode adhesion and the quality of cardiac signal recordings. Furthermore, the physical movements of the patient and their clothing impart various compressional, tensile, bending, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions.

While subcutaneous ECG monitors can perform monitoring for an extended period of time, up to three years, such subcutaneous ECG monitors, because of their small size, have greater problems of demonstrating a clear and dependable P-wave. The issues related to a tiny atrial voltage are exacerbated by the small size of insertable cardiac monitors (ICMs), the signal processing limits imposed upon them by virtue of their reduced electrode size, and restricted inter-electrode spacing. Conventional subcutaneous ICMs, as well as most conventional surface ECG monitors, are notorious for poor visualization of the P-wave, which remains the primary reason that heart rhythm disorders cannot precisely be identified today from ICMs. Furthermore, even when physiologically present, the P-wave may not actually appear on an ECG because the P-wave's visibility is strongly dependent upon the signal capturing ability of the ECG recording device's sensing circuitry. This situation is further influenced by several factors, including electrode configuration, electrode surface areas and shapes, inter-electrode spacing; where the electrodes are placed on or within the body relative to the heart's atria. Further, the presence or absence of ambient noise and the means to limit the ambient noise is a key aspect of whether the low amplitude atrial signal can be seen.

Conventional ICMs are often used after diagnostic measures when dermal ECG monitors fail to identify a suspected arrhythmia. Consequently, when a physician is strongly suspicious of a serious cardiac rhythm disorder that may have caused loss of consciousness or stroke, for example, the physician will often proceed to the insertion of an ICM under the skin of the thorax. Although traditionally, the quality of the signal is limited with ICMs with respect to identifying the P-wave, the duration of monitoring is hoped to compensate for poor P-wave recording. This situation has led to a dependence on scrutiny of R-wave behavior, such as RR interval (R-wave-to-R-wave interval) behavior, often used as a surrogate for diagnosing atrial fibrillation, a potential cause of stroke. To a limited extent, this approach has some degree of value. Nevertheless, better recording of the P-wave would result in a significant diagnostic improvement, not only in the case of atrial fibrillation, but in a host of other rhythm disorders that can result in syncope or loss of consciousness, like VT or heart block.

As mentioned above, the P-wave is the most difficult ECG signal to capture by virtue of originating in the low tissue mass atria and having both low voltage amplitude and relatively low frequency content. Notwithstanding these physiological constraints, ICMs are popular, albeit limited in their diagnostic yield. The few ICMs that are commercially available today, including the Reveal LINQ ICM, manufactured by Medtronic, Inc., Minneapolis, Minn., the BioMonitor 2 (AF and S versions), manufactured by Biotronik SE & Co. KG, Berlin, Germany, and the Abbott Confirm Rx ICM, manufactured by Abbott Laboratories, Chicago, Ill., all are uniformly limited in their abilities to clearly and consistently sense, record, and deliver the P-wave.

Typically, the current realm of ICM devices use a loop recorder where cumulative ECG data lasting for around an hour is continually overwritten unless an episode of pre-programmed interest occurs or a patient marker is manually triggered. The limited temporal window afforded by the recordation loop is yet another restriction on the evaluation of the P-wave, and related cardiac morphologies, and further compromises diagnostic opportunities.

For instance, Medtronic's Reveal LINQ ICM delivers long-term subcutaneous ECG monitoring for up to three years, depending on programming. The monitor is able to store up to 59 minutes of ECG data, include up to 30 minutes of patient-activated episodes, 27 minutes of automatically detected episodes, and two minutes of the longest atrial fibrillation (AF) episode stored since the last interrogation of the device. The focus of the device is more directed to recording duration and programming options for recording time and patient interactions rather than signal fidelity. The Reveal LINQ ICM is intended for general purpose ECG monitoring and lacks an engineering focus on P-wave visualization. Moreover, the device's recording circuitry is intended to secure the ventricular signal by capturing the R-wave, and is designed to accommodate placement over a broad range of subcutaneous implantation sites, which is usually sufficient if one is focused on the R-wave given its amplitude and frequency content, but of limited value in capturing the low-amplitude, low-frequency content P-wave. Finally, electrode spacing, surface areas, and shapes are dictated (and limited) by the physical size of the monitor's housing which is quite small, an aesthetic choice, but unrealistic with respect to capturing the P-wave.

Similar in design is the titanium housing of Biotronik's BioMonitor 2 but with a flexible silicone antenna to mount a distal electrode lead, albeit of a standardized length. This standardized length mollifies, in one parameter only, the concerns of limited inter-electrode spacing and its curbing effect on securing the P-wave. None of the other factors related to P-wave signal revelation are addressed. Therefore the quality of sensed P-waves reflects a compromise caused by closely-spaced poles that fail to consistently preserve P-wave fidelity, with the reality of the physics imposed problems of signal-to-noise ratio limitations remaining mostly unaddressed.

Therefore, a need remains for a way to capture low amplitude cardiac action potential propagation during long term cardiac monitoring and to present R-R interval data to physicians to reveal temporally-related patterns as an aid to rhythm abnormality diagnosis.

SUMMARY

R-R interval data is presented to physicians in a format that includes views of relevant near field and far field ECG data, which together provide contextual information that improves diagnostic accuracy. The near field (or short duration) ECG data view provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view.

Both near field and far field ECG data views are temporally keyed to an extended duration R-R interval data view. In one embodiment, the R-R interval data view is scaled non-linearly to maximize the visual differentiation for frequently-occurring heart rate ranges, such that a single glance allows the physician to make a diagnosis. All three views are presented simultaneously, thereby allowing an interpreting physician to diagnose rhythm and the pre- and post-contextual events leading up to a cardiac rhythm of interest.

The durations of the classical "pinpoint" view, the pre- and post-event "intermediate" view, and the R-R interval plot are flexible and adjustable. In one embodiment, a temporal point of reference is identified in the R-R interval plot and the ECG data that is temporally associated with the point of reference is displayed in the near field and far field ECG data views. In a further embodiment, diagnostically relevant cardiac events can be identified as the temporal point of reference. For clarity, the temporal point of reference will generally be placed in the center of the R-R interval data to allow pre- and post-event heart rhythm and ECG waveform data to present in the correct context. Thus, the pinpoint "snapshot" and intermediate views of ECG data with the extended term R-R interval data allow a physician to comparatively view heart rate context and patterns of behavior prior to and after a clinically meaningful arrhythmia, patient concern or other indicia, thereby enhancing diagnostic specificity of cardiac rhythm disorders and providing physiological context to improve diagnostic ability.

The ECG data from which the R-R interval plot is created can be obtained through a continuously-recording subcutaneous insertable cardiac monitor (ICM), such as one described in commonly-owned U.S. patent application Ser. No. 15/832,385, filed Dec. 5, 2017, pending, the disclosure of which is incorporated by reference. The sensing circuitry and the physical layout of the electrodes are specifically optimized to capture electrical signals from the propagation of low amplitude, relatively low frequency content cardiac action potentials, particularly the P-waves that are generated during atrial activation. In general, the ICM is intended to be implanted centrally and positioned axially and slightly to either the left or right of the sternal midline in the parasternal region of the chest.

In one embodiment, a system and method for facilitating a cardiac rhythm disorder diagnosis based on subcutaneous cardiac monitoring data. Cardiac action potentials of a patient over a set time period are recorded using an implantable housing comprised of a biocompatible material that is suitable for implantation within a living body; at least one pair of electrocardiographic (ECG) sensing electrodes provided on a ventral surface and on opposite ends of the implantable housing operatively placed to facilitate sensing in closest proximity to the low amplitude, low frequency content cardiac action potentials that are generated during atrial activation; and electronic circuitry provided within the housing assembly comprising a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals. The stored samples of the ECG signals as ECG data are retrieved. A set of R-wave peaks within the ECG data are identified. An R-R interval plot is constructed, including determining a difference between recording times of successive pairs of the R-wave peaks in the set; determining a heart rate associated with each difference; and plotting the pairs of the R-wave peaks and associated heart rate as the R-R interval plot. Diagnosis of a cardiac disorder of the patient based on patterns of the plotted pairs of the R-wave peaks and the associated heart rates in the R-R interval plot is facilitated. The foregoing aspects enhance the presentation of diagnostically relevant R-R interval data, reduce time and effort needed to gather relevant information by a clinician and provide the clinician with a concise and effective diagnostic tool, which is critical to accurate arrhythmia and cardiac rhythm disorder diagnoses.

Custom software packages have been used to identify diagnostically relevant cardiac events from the electrocardiography data, but usually require a cardiologist's diagnosis and verification. In contrast, when presented with a machine-identified event, the foregoing approach aids the cardiologist's diagnostic job by facilitating presentation of ECG-based background information prior to and after the identified event.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

DETAILED DESCRIPTION

A normal healthy cardiac cycle repeats through an expected sequence of events that can be visually traced through an ECG. Each cycle starts with cardiac depolarization originating high in the right atrium in the sinoatrial (SA) node before spreading leftward towards the left atrium and inferiorly towards the atrioventricular (AV) node. After a delay in the AV node, the depolarization impulse transits the Bundle of His and moves into the right and left bundle branches and Purkinje fibers to activate the right and left ventricles.

Figure 1:
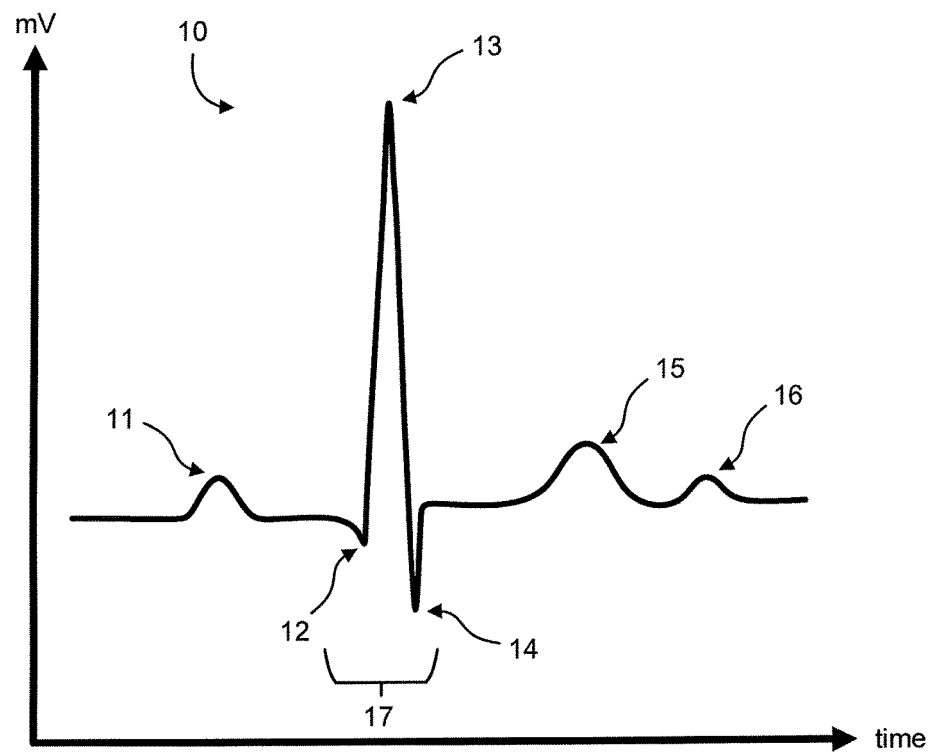
FIG. 1 is a graph showing, by way of example, a single ECG waveform.

When a rhythm disorder is suspected, diagnostically-relevant arrhythmic events in the cardiac cycle can often be identified and evaluated with the assistance of an ECG and R-R interval tachography, such as Poincaré plots. Routine ECG evaluation is primarily focused identifying changes to expected ECG waveform shapes. FIG. 1 is a graph showing, by way of example, a single ECG waveform 10. The x-axis represents approximate time in units of tenths of a second and the y-axis represents approximate cutaneous electrical signal strength in units of millivolts. By long-standing convention, ECGs are typically printed or displayed at an effective paper speed of 25 millimeters (mm) per second. Although in practice an ECG may be provided to a physician in traditional paper-printed form, in "virtual" electronic display form, or both, the term "effective paper speed" is nevertheless still widely applied as a metric to normalize the recorded ECG signal to a standardized grid of 1 mm squares (omitted for the sake of clarity in FIG. 1), whereby each 1 mm horizontal box in the grid corresponds to 0.04 s (40 ms) of recorded time. Other effective paper speeds, grid sizes and units of display are possible.

A full ECG consists of a stream of alphabetically-labeled waveforms 10 that collectively cover cardiac performance over a period of observation. For a healthy patient, within each ECG waveform 10, the P-wave 11 will normally have a smooth, normally upward, positive waveform that indicates atrial depolarization. The QRS complex 17 will usually follow, often with a downward deflection of a Q-wave 12, followed by a larger upward deflection of an R-wave 13, and be terminated with a downward waveform of the S-wave 14, which are collectively representative of ventricular depolarization. The T-wave 15 will normally be a modest upward waveform, representative of ventricular repolarization, while the U-wave 16, which is often not directly observable, will indicate the recovery period of the Purkinje conduction fibers.

Rhythm disorders often manifest through R-R interval variability and the patterns formed by R-R intervals over an extended time period are important tools in the diagnosis of cardiac rhythm abnormalities. For example, atrial fibrillation (AF) is the chaotic firing of the atria that leads to an erratic activation of the ventricles. AF is initially diagnosed by an absence of organized P-waves 11 and confirmed by erratic ventricular rates that manifest in an ECG R-R interval plot as a cloud-like pattern of irregular R-R intervals due to an abnormal conduction of impulses to the ventricles. There is a Gaussian-like distribution to these R-R intervals during AF. Similarly, atrial flutter (AFL) is an abnormal heart rhythm in which cardiac impulses travel along pathways within the right atrium in an organized circular motion, causing the atria to beat faster than and out of sync with the ventricles. During AFL, the heart beats quickly, yet with a regular pattern. Although AFL presents in an electrogram (e-gram) as a "sawtooth" pattern, AFL can be confirmed in an ECG by characteristic R-R interval patterns that usually manifest as 2:1 atrioventricular (AV) conduction or 4:1 atrioventricular conduction. On occasion, the conduction through the AV node is variable and not fixed.

Figure 2:
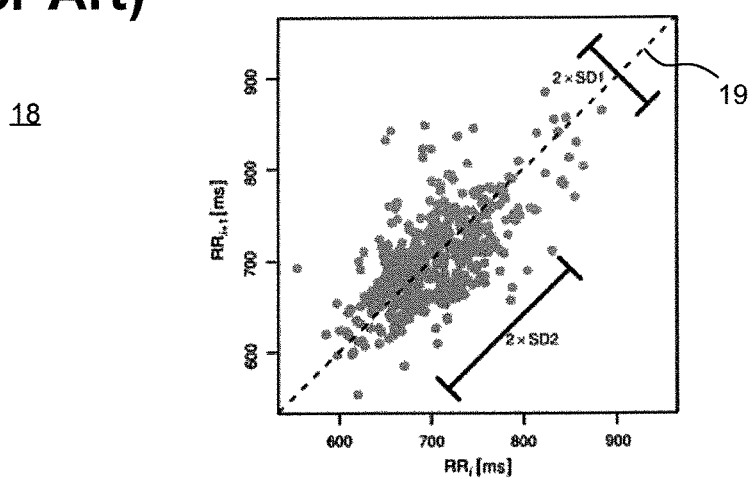
FIG. 2 is a graph showing, by way of example, a prior art Poincaré R-R interval plot.

Conventionally, R-R intervals have been visualized using Poincare plots. FIG. 2 is a graph showing, by way of example, a prior art Poincare R-R interval plot 18. The x-axis represents the duration of R-R interval n in units of milliseconds (ms). The y-axis represents the duration of R-R interval n+1 also in units of ms. Ordinarily, the x- and y-axes use the same units, so as to form a trend line 19 along the 45-degree angle. When an R-R interval is equal to the successive R-R interval, as often occurs when heart rhythm is regular, the dot representing the two intervals falls onto the 45-degree trend line 19. Conversely, when an R-R interval has changed since the preceding R-R interval, the dot representing the two intervals falls off the 45-degree trend line 19 and, as the difference between successive R-R intervals increases, the dots fall further away from the trend line 19.

The number of dots deviating from the trend line 19 in a Poincare plot can indicate the frequency of occurrence of irregular heartbeats when compared to the number of dots on the trend line 19. The distance of the dots to the trend line 19 can approximate the extent of heart rate change from one heartbeat to the next. However, as heart rate change is limited to only successively-occurring heartbeats, the linearity of time and associated contextual information over an extended time frame are lost. In addition, significant changes in heart rate, particularly spikes in heart rate, such as due to sinus rhythm transitions to atrial flutter, may be masked, distorted or even omitted in a Poincare plot if the change occurs over non-successive heartbeats. In summary, a Poincare plot is more useful as a mathematical tool than a physiological one, and therefore a Poincare plot cannot truly represent what the heart is doing serially over time with respect to changes in the heart's normal and abnormal physiology.

Figure 3:
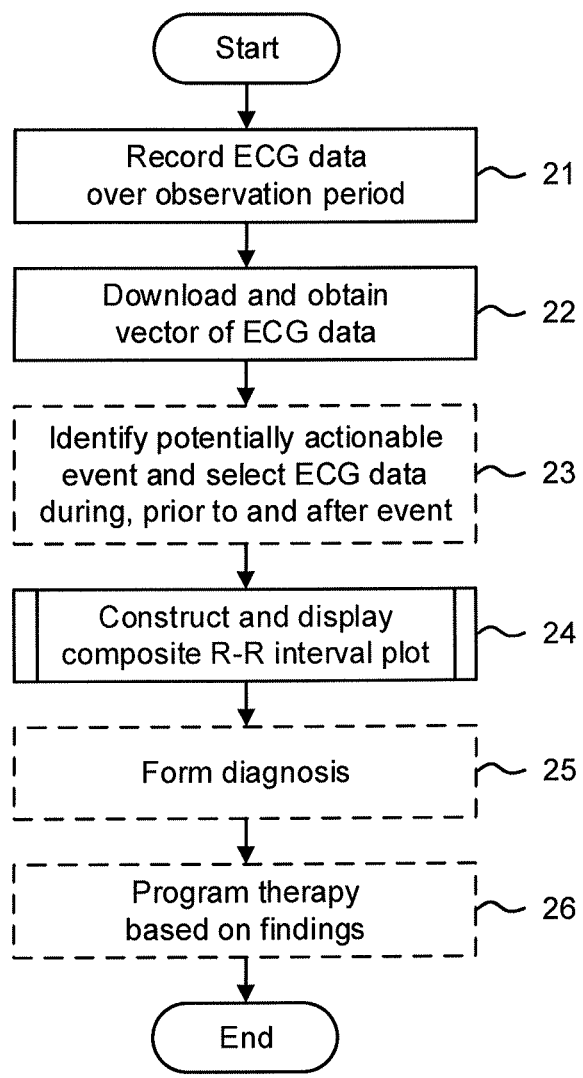
FIG. 3 is a flow diagram showing a method for facilitating diagnosis of cardiac rhythm disorders with the aid of a digital computer in accordance with one embodiment.

Despite the limitations of Poincare plots and related forms of R-R interval tachography, R-R interval data when presented in a format duplicating temporal physiological events remains a key tool that physicians can rely upon to identify temporally-related cardiac dysrhythmic patterns. Interpretation of R-R interval data can be assisted by including multiple temporal points of reference and a plot of R-R interval data that comparatively depicts heart rate variability in concert with R-R interval data. FIG. 3 is a flow diagram showing a method 20 for facilitating diagnosis of cardiac rhythm disorders with the aid of a digital computer in accordance with one embodiment. The method 20 can be implemented in software and execution of the software can be performed on a computer, such as further described infra with reference to FIG. 14, as a series of process or method modules or steps.

As a precursor step, the cutaneous action potentials of a patient are monitored and recorded as ECG data over a set time period (step 21), which can be over a short term or extended time frame. ECG recordation, as well as physiological monitoring, can be provided through various kinds of ECU-capable monitoring ensembles, including a standardized 12-lead ECG setup, such as used for clinical ECG monitoring, a portable Holter-type ECG recorder for traditional ambulatory ECG monitoring, or a wearable ambulatory ECG monitor, such as a flexible extended wear electrode patch and a removable reusable (or single use) monitor recorder, such as described in commonly-assigned U.S. Pat. No. 9,345,414, issued May 24, 2016, the disclosure of which is incorporated by reference, the latter of which includes an electrode patch and monitor recorder that are synergistically optimized to capture electrical signals from the propagation of low amplitude, relatively low frequency content cardiac action potentials, particularly the P-waves, generated during atrial activation. Still other forms of ECG monitoring assembles are possible.

Figure 14:
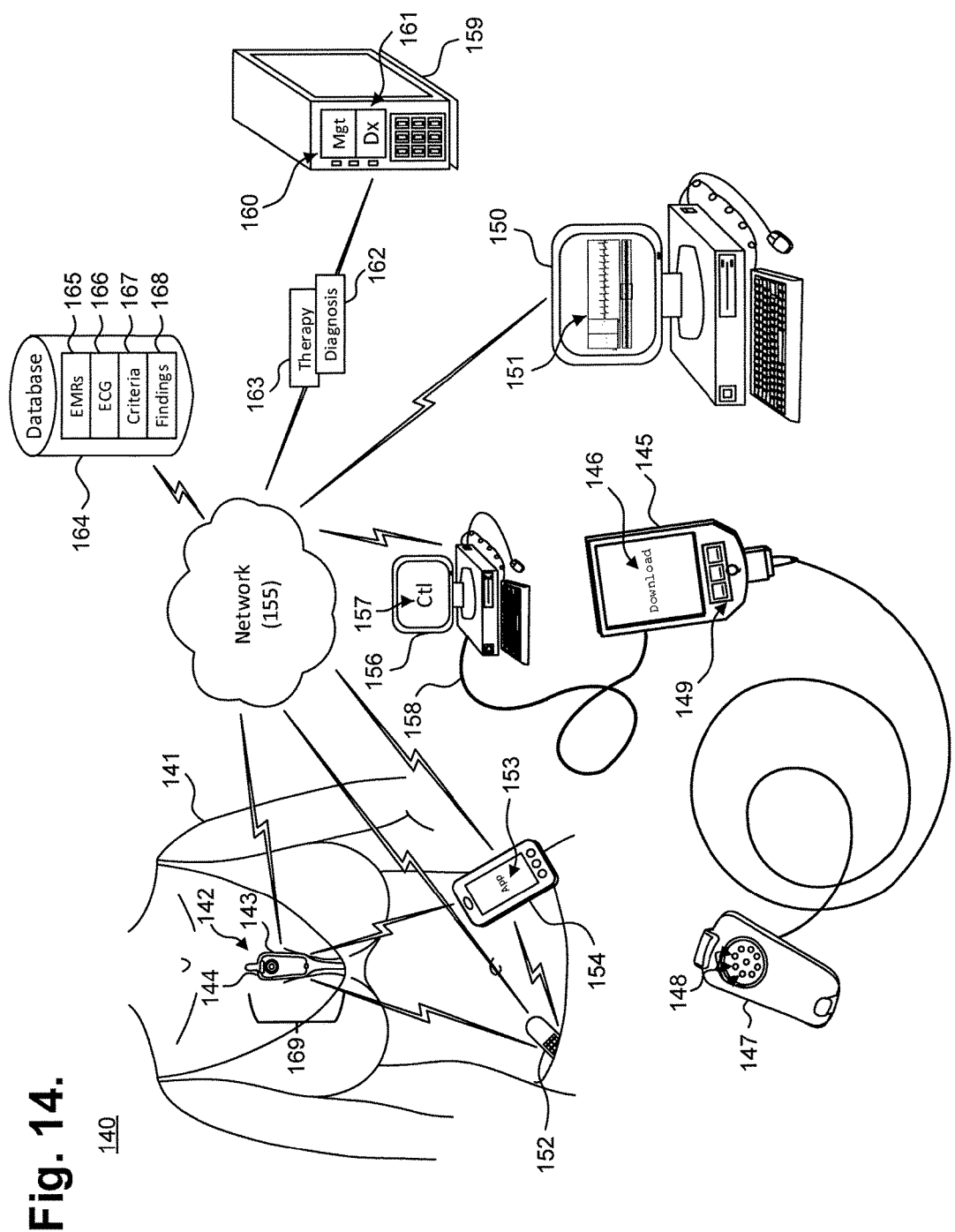
FIG. 14 is a block diagram showing a system for facilitating diagnosis of cardiac rhythm disorders with the aid of a digital computer in accordance with one embodiment.

Upon completion of the monitoring period, the ECG and any physiological data are downloaded or retrieved into a digital computer, as further described infra with reference to FIG. 14, with, for instance, the assistance of a download station or similar device, or via wireless connection, if so equipped, and a vector of the downloaded or retrieved ECG data is obtained (step 22). In one embodiment, the vector of ECG data represents a 40-minute (or other duration) time span that is used in constructing the plot of R-R interval data, although other pre-event and post-event time spans are possible. Optionally, a potentially-actionable cardiac event within the vector of ECG data can be identified and the ECG data during, prior to and after the event is selected (step 23). The event could be identified with the assistance of a software package, such as Holter LX Analysis Software, licensed by NorthEast Monitoring, Inc., Maynard, Mass.; IntelliSpace Cardiovascular Image and Information management system, licensed Koninklijke Philips N.V., Amsterdam, Netherlands; MoMe System, licensed by InfoBionic, Lowell, Mass.; Pyramis ECG Management, licensed by Mortara Instrument Inc., Milwaukee, Wis.; ICS Clinical Suite, licensed by Spacelabs Healthcare Inc., Snoqualmie, Wash.; or a customized software package. Alternatively, the potentially-actionable cardiac event could be identified by a physician or technician during review of the ECG data.

Figure 4:
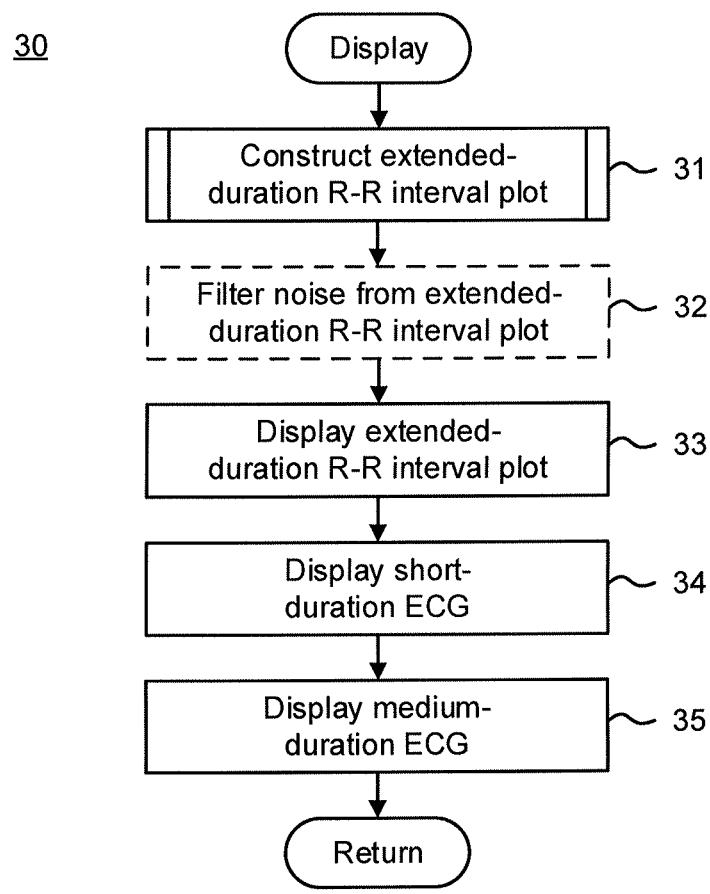
FIG. 4 is a flow diagram showing a routine for constructing and displaying a diagnostic composite plot for use in the method of FIG. 3.

To improve diagnosis of heart rate variability, a diagnostic composite plot is constructed that includes one or more temporal points of reference into the ECG data, which provide important diagnostic context, and a plot of R-R interval data is constructed based on the vector of ECG data (step 24), as further described infra with reference to FIG. 4. Briefly, both near field and far field contextual views of the ECG data are constructed and displayed. Both views are temporally keyed to an extended duration R-R interval data view that, in one embodiment, is scaled non-linearly to maximize the visual differentiation for frequently-occurring heart rate ranges, such that a single glance allows the physician to make a diagnosis. All three views are presented simultaneously, thereby allowing the interpreting physician to diagnose rhythm and the pre- and post-contextual events leading up to a cardiac rhythm of interest.

In a further embodiment, findings made through interpretation of heart rate variability patterns in the diagnostic composite plot can be analyzed to form a diagnosis of a cardiac rhythm disorder (step 25), such as the cardiac rhythm disorders listed, by way of example, in Table 1. For instance, the heart rate variability patterns in the diagnostic composite plot could be provided to a system that programmatically detects AF by virtue of looking for the classic Gaussian-type distribution on the "cloud" of heart rate variability formed in the plot of R-R interval data, which can be corroborated by the accompanying contextual ECG data. Finally, therapy to address diagnosed disorder findings can optionally be programmed into a cardiac rhythm therapy delivery device (step 26), such as an implantable medical device (IMD) (not shown), including a pacemaker, implantable cardioverter defibrillator (ICD), or similar devices.

TABLE 1

Cardiac Rhythm Disorders

Normal sinus rhythm
Sinus Bradycardia
Sinus Tachycardia
Premature atrial and ventricular beats
Ectopic atrial tachycardia
Atrial fibrillation
Atrial flutter
Atrial or ventricular bigeminy, trigeminy or quadrigeminy
Sinus Bradycardia
Fusion beats
Interpolated ventricular premature beats
Intraventricular conduction delay
Junctional rhythm
AV Nodal re-entrant tachycardia
AV re-entrant tachycardia
Wolff-Parkinson-White Syndrome and Pre-excitation
Ventricular tachycardia
Accelerated idioventricular rhythm
AV Wenckebach block
AV Type II block
Sinoatrial block A diagnostic composite plot is constructed and displayed to help physicians identify and diagnose temporally-related cardiac dysrhythmic patterns. The diagnostic composite plot includes ECG traces from two or more temporal points of reference and a plot of R-R interval data, although other configurations of ECG data plots when combined with the R-R interval plot will also provide critical information. FIG. 4 is a flow diagram showing a routine 30 for constructing and displaying a diagnostic composite plot for use in the method 20 of FIG. 3. Specific examples of diagnostic composite plots are discussed in detail infra with reference to FIGS. 7-13.

In the diagnostic composite plot, R-R interval data is presented to physicians in a format that includes views of relevant near field and far field ECG data, which together provide contextual information that improves diagnostic accuracy. In a further embodiment, other views of ECG data can be provided in addition to or in lieu of the near field and far field ECG data views. The near field (or short duration) ECG data provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view. Thus, the extended-duration R-R interval plot is first constructed (step 31), as further described infra with reference to FIG. 5. Optionally, noise can be filtered from the R-R interval plot (step 32), which is then displayed (step 33). Noise filtering can include low-pass or high-pass filtering or other forms of signal processing, including automatic gain control, such as described in commonly-assigned U.S. patent application Ser. No. 14/997,416, cited supra.

Rhythm disorders have different weightings depending upon the context with which they occur. In the diagnostic composite plot, the R-R interval data view and the multiple views of the ECG data provide that necessary context. Effectively, the short and medium duration ECG data that accompanies the extended-duration R-R interval plot represents the ECG data "zoomed" in around a temporal point of reference identified in the center (or other location) of the R-R interval plot, thereby providing a visual context to the physician that allows temporal assessment of cardiac rhythm changes in various complementary views of the heart's behavior. The durations of the classical "pinpoint" view, the pre- and post-event "intermediate" view, and the R-R interval plot are flexible and adjustable. In one embodiment, the diagnostic composite plot displays R-R interval data over a forty-minute duration and ECG data over short and medium durations (steps 34 and 35), such as four-second and 24-second durations that provide two- and 12-second segments of the ECG data before and after the R-R interval plot's temporal point of reference, which is generally in the center of the R-R interval plot, although other locations in the R-R interval plot could be identified as the temporal point of reference. The pinpoint "snapshot" and intermediate views of ECG data with the extended term R-R interval data comparatively depicts heart rate context and patterns of behavior prior to and after a clinically meaningful arrhythmia or patient concern, thereby enhancing diagnostic specificity of cardiac rhythm disorders and providing physiological context to improve diagnostic ability. In a further embodiment, diagnostically relevant cardiac events can be identified and the R-R interval plot can be constructed with a cardiac event centered in the middle (or other location) of the plot, which thereby allows pre- and post-event heart rhythm data to be contextually "framed" through the pinpoint and intermediate ECG data views. Other durations, intervals and presentations of ECG data are possible.

Figure 5:
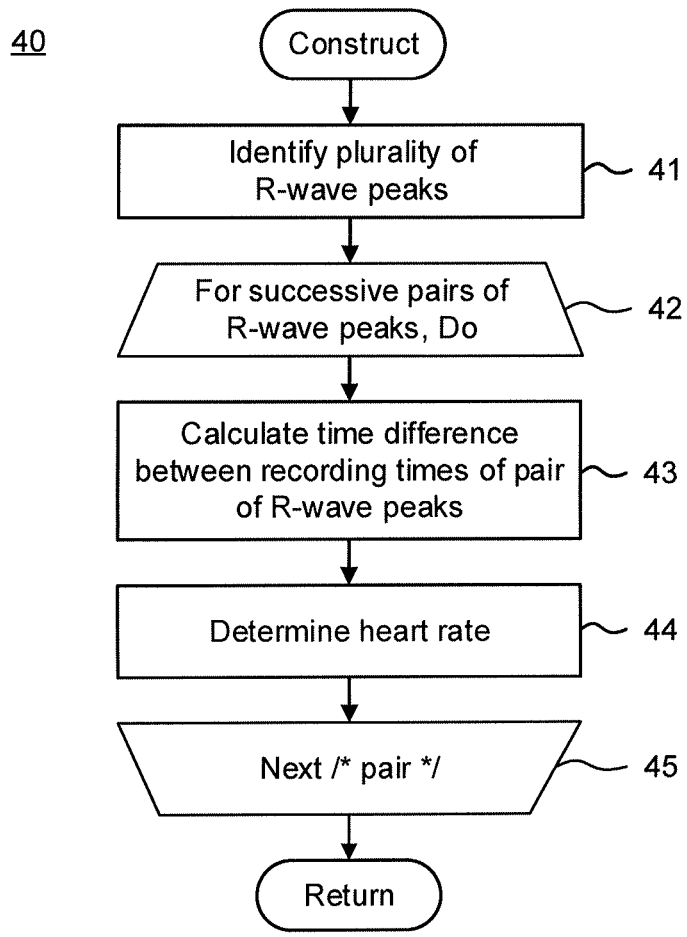
FIG. 5 is a flow diagram showing a routine for constructing an extended-duration R-R interval plot for use in the routine of FIG. 4.

The extended-duration R-R interval plot presents beat-to-beat heart rate variability in a format that is intuitive and contextual, yet condensed. The format of the R-R interval plot is selected to optimize visualization of cardiac events in a compressed, yet understandable field of view, that allows for compact presentation of the data akin to a cardiologists understanding of clinical events. FIG. 5 is a flow diagram showing a routine 40 for constructing an extended-duration R-R interval plot for use in the routine 30 of FIG. 4. The duration of the R-R interval plot can vary from less than one minute to the entire duration of the recording. Thus, a plurality of R-wave peaks is first selected out of the vector of ECG data (step 41) appropriate to the duration of the R-R interval plot to be constructed. For successive pairs of the R-wave peaks (steps 42-43), the difference between the recording times of the R-peaks is calculated (step 43). Each recording time difference represents the length of one heartbeat. The heart rate associated with the recording time difference is determined by taking an inverse of the recording time difference and normalizing the inverse to beats per minute (step 44). Taking the inverse of the recording time difference yields a heart rate expressed in beats per second, which can be adjusted by a factor of 60 to provide a heart rate expressed in bpm. Calculation of the differences between the recording times and the associated heart rate continues for all of the remaining pairs of the R-wave peaks (step 44).

The pairings of R-R intervals and associated heart rates are formed into a two-dimensional plot. R-R intervals are plotted along the x-axis and associated heart rates are plotted along the y-axis. The range and scale of the y-axis (heart rate) can be adjusted according to the range and frequency of normal or patient-specific heart rates, so as to increase the visual distinctions between the heart rates that correspond to different R-R intervals. In one embodiment, the y-axis of the R-R interval plot has a range of 20 to 300 beats per minute and R-R intervals corresponding to heart rates falling extremely outside of this range are excluded to allow easy visualization of 99+% of the heart rate possibilities.

In a further embodiment, the y-axis has a non-linear scale that is calculated as a function of the x-axis (R-R interval), such that:

$$y = \left(\frac{x - \text{min bpm}}{\text{max bpm} - \text{min bpm}}\right)^n$$

where x is the time difference, min bpm is the minimum heart rate, max bpm is the maximum heart rate, and n<1. The non-linear scale of the y-axis accentuates the spatial distance between successive heart rates when heart rate is low. For example, when n=2, the spatial difference between 50 and 60 bpm is 32% larger than the spatial difference between 90 bpm and 100 bpm, and 68% larger than the spatial difference between 150 bpm and 160 bpm. As a result the overall effect is to accentuate the spatial differences in frequently-occurring ranges of heart rate and de-emphasize the spatial differential in ranges of heart rate where a deviation from norm would have been apparent, thus maximizing the spatial efficiency in data presentation. The goal is to show cardiac events in a simple, small visual contextual format. Larger scales and larger formats bely the practical limits of single-page presentations for the easy visualization at a glance by the busy physician. The visual distinctions between the heart rates that correspond to different R-R intervals stand out, especially when plotted on a non-linear scale. Other y-axis ranges and scales are possible as may be selected by distinct clinical needs and specific diagnostic requirements.

Figure 6:
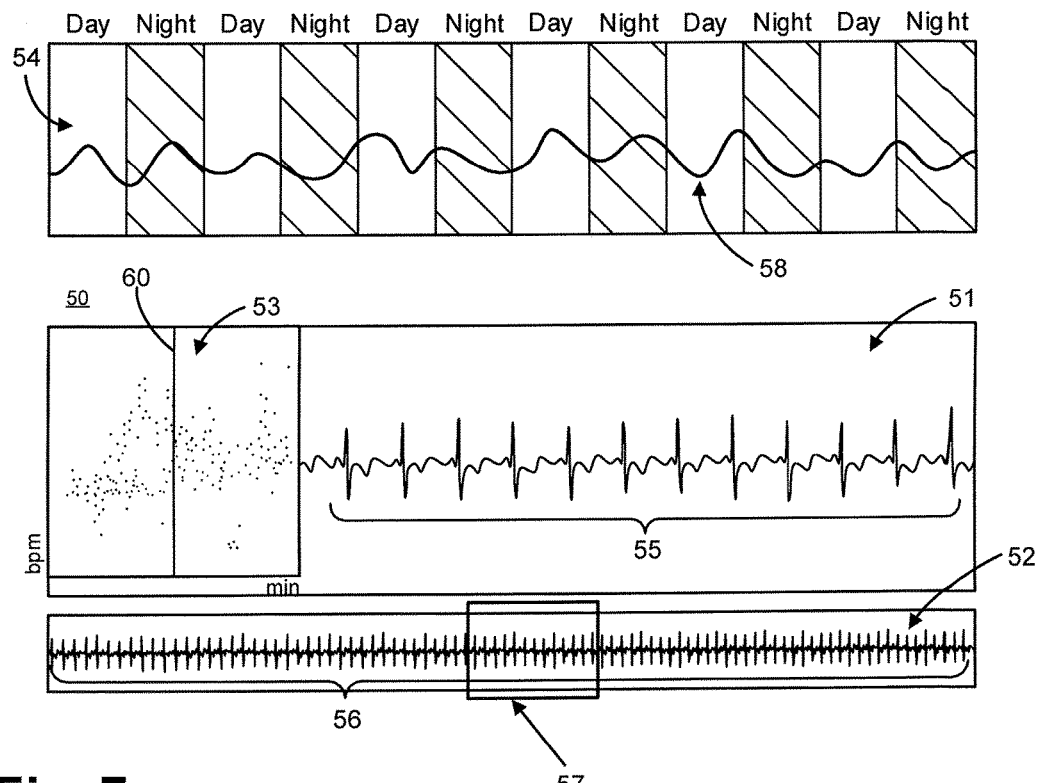
FIG. 6 is a diagram showing, by way of example, a diagnostic composite plot generated by the method of FIG. 3.

The diagnostic composite plot includes a single, long range view of R-R interval data and a pair of pinpoint ECG data views that together help to facilitate rhythm disorder diagnosis by placing focused long-term heart rate information alongside short-term and medium-term ECG information. Such pairing of ECG and R-R interval data is unique in its ability to inform the physician of events prior to, during and after a cardiovascular event. FIG. 6 is a diagram showing, by way of example, a diagnostic composite plot 50 generated by the method 30 of FIG. 3. Note that the diagnostic composite plot can be tailored to include more than one view of R-R interval data and as many views of contextual ECG data as needed. In a further embodiment, a background information plot presenting an extended far field of related information can be included, such as activity amount, activity intensity, posture, syncope impulse detection, respiratory rate, blood pressure, oxygen saturation ($SpO_2$), blood carbon dioxide level ($pCO_2$), glucose, lung wetness, and temperature. Other forms of background information are possible. In a still further embodiment, background information can be layered on top of or keyed to the diagnostic composite plot 50, particularly at key points of time in the R-R interval data plot, so that the context provided by each item of background information can be readily accessed by the reviewing physician.

The diagnostic composite plot 50 includes an ECG plot presenting a near field (short duration) view 51, an ECG plot presenting an intermediate field (medium duration) view 52, and an R-R interval data plot presenting a far field (extended duration) view 53. The three views 51, 52, 53 are juxtaposed alongside one other to allow quick back and forth referencing of the full context of the heart's normal and abnormal physiology. Typically, a temporal point of reference, which could be a diagnostically relevant cardiac event, patient concern or other indicia, would be identified and centered on the x-axis in all three views. The placement of the temporal point of reference in the middle of all three x-axes enables the ECG data to be temporally keyed to the R-R interval data appearing in the center 60 of the R-R interval data view 53, with a near field view 51 of an ECG displayed at normal (paper-based) recording speed and a far field view 52 that presents the ECG data occurring before and after the center 60. As a result, the near field view 51 provides the ECG data corresponding to the R-R interval data at the center 60 (or other location) in a format that is familiar to all physicians, while the intermediate field view 52 enables presentation of the broader ECG data context going beyond the borders of the near field view 51. In a further embodiment, the center 60 can be slidably adjusted backwards and forwards in time, with the near field view 51 and the far field view 52 of the ECG data automatically adjusting accordingly to stay in context with the R-R interval data view 51. In a still further embodiment, multiple temporal points of reference can be identified with each temporal point of reference being optionally accompanied by one or more dedicated sets of ECG data views.

The collection of plots are conveniently arranged close enough to one another to facilitate printing on a single page of standard sized paper (or physical paper substitute, such as a PDF file), although other layouts of the plots are possible. The far field view 53 is plotted with time in the x-axis and heart rate in the y-axis. The R-R intervals are calculated by measuring the time occurring between successive R-wave peaks. In one embodiment, the far field view 53 presents R-R interval data (expressed as heart rate in bpm) that begins about 20 minutes prior to and ends about 20 minutes following the center 60, although other durations are possible.

The near field view 51 and intermediate field view 52 present ECG data relative to the center 60 of the far field view 53. The near field view 51 provides a pinpoint or short duration view of the ECG data. In one embodiment, the near field view 51 presents ECG data 55 that begins about two seconds prior to and ends about two seconds following the center 60, although other durations are possible. The intermediate field view 52 provides additional contextual ECG information allowing the physician to assess the ECG itself and gather a broader view of the rhythm before and after a "blow-up" of the specific arrhythmia of interest. In one embodiment, the intermediate field view 52 presents ECG data 56 that begins about 12 seconds prior to and ends about 12 seconds following the center 60, although other durations are possible. For convenience, the eight-second interval of the ECG data 56 in the intermediate field view 52 that makes up the ECG data 56 in the near field view 51 is visually highlighted, here, with a surrounding box 57. In addition, other views of the ECG data, either in addition to or in lieu of the near field view 51 and the far field view 52 are possible. Optionally, an ECG plot presenting an extended far field view 54 of the background information can be included in the diagnostic composite plot 50. In one embodiment, the background information is presented as average heart rate with day and night periods 58 alternately shaded along the x-axis. Other types of background information, such as activity amount, activity intensity, posture, syncope impulse detection, respiratory rate, blood pressure, oxygen saturation ($SpO_2$), blood carbon dioxide level ($pCO_2$), glucose, lung wetness, and temperature, are possible.

Figure 7:
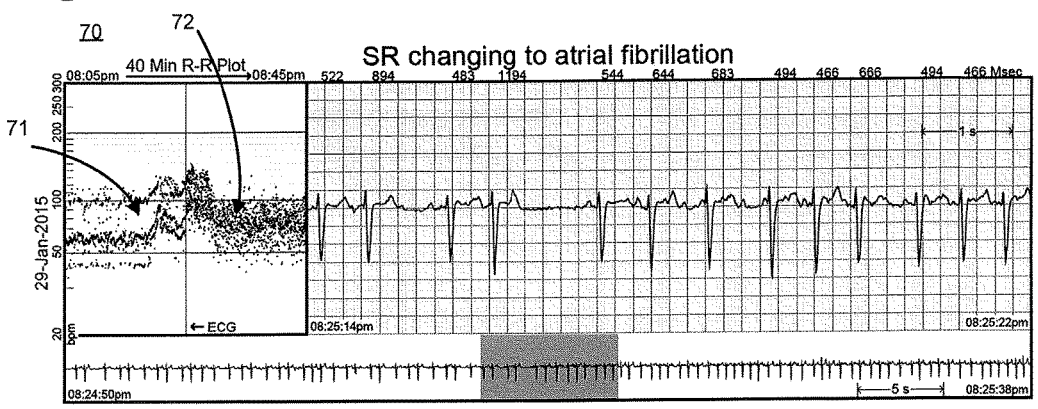
FIG. 7 is a diagram showing, by way of example, a diagnostic composite plot for facilitating the diagnosis of sinus rhythm (SR) transitioning into atrial fibrillation (AF).

Examples of the diagnostic composite plot as applied to specific forms of cardiac rhythm disorders will now be discussed. These examples help to illustrate the distinctive weightings that accompany different forms of rhythm disorders and the R-R interval and ECG waveform deflection context with which they occur. FIG. 7 is a diagram showing, by way of example, a diagnostic composite plot 70 for facilitating the diagnosis of sinus rhythm (SR) transitioning into AF. SR is indicated through the presence of a reasonably steady baseline, but with subsidiary lines of premature beats and their compensatory pauses. SR manifests as a shadowing 71 of a high heart rate line and a low heart rate line. AF is characterized by irregular heartbeats with a somewhat random variation of R-R intervals, although within a limited range and concentrating in a Gaussian-like distribution pattern around a mean that varies over time. Although AF can be diagnosed by viewing a near field view 51 of ECG data showing heartbeats with reversed P-wave and irregular R-R intervals, this approach may be unclear when viewing "snippets" of ECG data, especially when associated with poor quality ECG signals. The presence of AF can also be confirmed through a far field view 53 of R-R interval data, in which the R-R intervals assume superficially appearing disorganized, spread-out and decentralized scattered cloud 72 along the x-axis, in comparison to a concentrated, darkened line typical of a more organized cardiac rhythm.

Figure 8:
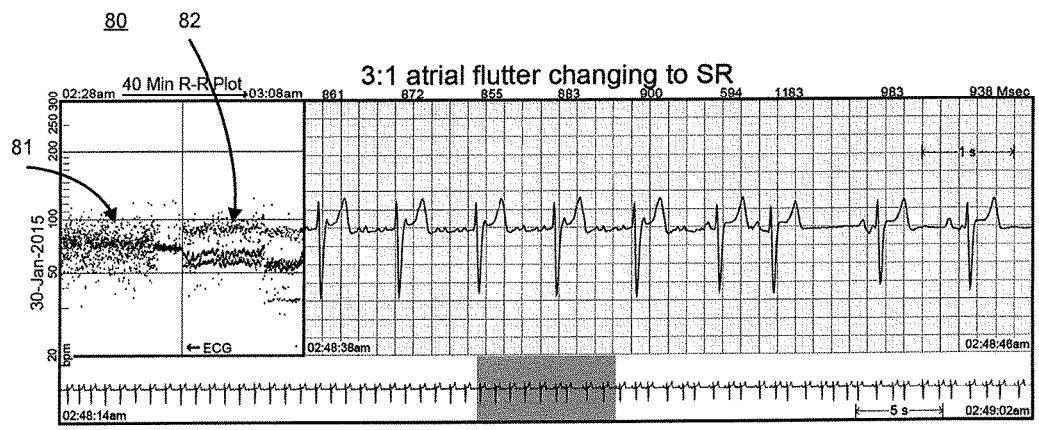
FIG. 8 is a diagram showing, by way of example, a diagnostic composite plot for facilitating the diagnosis of 3:1 atrial flutter (AFL) transitioning into SR.

FIG. 8 is a diagram showing, by way of example, a diagnostic composite plot 80 for facilitating the diagnosis of 3:1 atrial flutter (AFL) transitioning into SR with frequent premature ectopic atrial beats. In the initial part of the R-R interval plot, the R-R intervals have a discernible aggregated line in the middle of the cloud 81 when the rhythm has yet to stabilize into a set pattern, not quite AF and not quite AFL. Immediately thereafter, a dense line representing firm 3:1 atrial flutter stabilizes the rhythm prior to the transition into SR associated with the presence of two seesawing baselines that result from frequent atrial ectopy causing short coupling intervals and then compensatory long coupling intervals. SR is indicated by the middle of the three lines with a low heart rate line consistent with the compensatory pause (long coupling interval) and a high heart rate line with the shortest coupling interval representing the series of atrial premature beats 82, and thus, at a faster heart rate.

Figure 9:
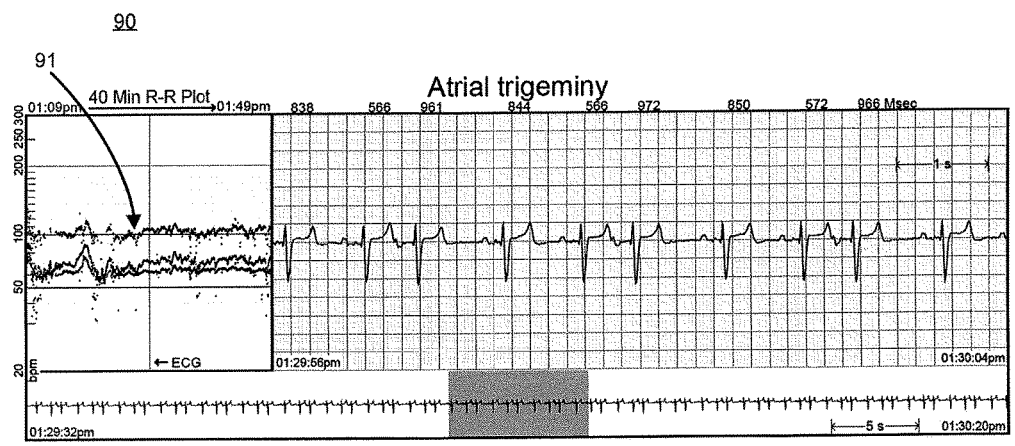
FIG. 9 is a diagram showing, by way of example, a diagnostic composite plot for facilitating the diagnosis of atrial trigeminy.

FIG. 9 is a diagram showing, by way of example, a diagnostic composite plot 90 for facilitating the diagnosis of atrial trigeminy. Atrial trigeminy is characterized by three heartbeat rates appearing intermittently yet reasonably regularly. Although atrial trigeminy can be diagnosed by viewing a near field view 51 of ECG data, the pattern is significantly more recognizable in a far field view 53 of R-R interval data, in which a repeating pattern of three distinct heartbeat lines are persistently present and clearly visible 91. This view also provides the physician with a qualitative feel for the frequency of the event troubling the patient that is not discernible from a single ECG strip.

Figure 10:
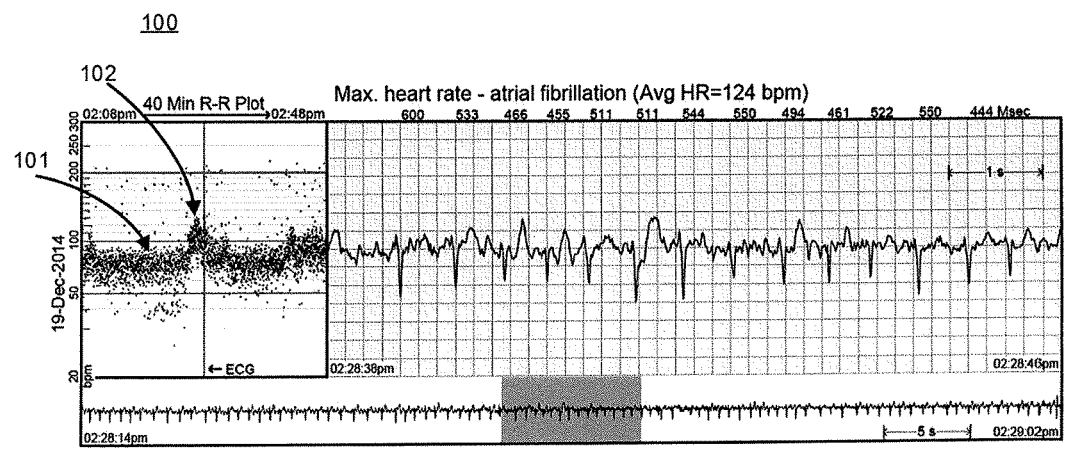
FIG. 10 is a diagram showing, by way of example, a diagnostic composite plot for facilitating the diagnosis of maximum heart rate in an episode of AF during exercise.

FIG. 10 is a diagram showing, by way of example, a diagnostic composite plot 100 for facilitating the diagnosis of maximum heart rate in an episode of AF during exercise. In a far field view 50 of R-R interval data, AF manifests through a dispersed cloud of dots (Gaussian-like distribution) without a discernible main heart rate line representing regular heartbeats 101. Under exercise, the maximum heartbeat can be located by an increase in heart rate clustered about the cloud 102. In addition, individual dots above the 200 bpm range throughout the entire 40-minute range indicates the maximum heart rate during exercise. The very rapid rise in heart rate can be critical to patient management, as such bumps in rate by exercise can prove serious and even trigger cardiac arrest. Their very presence is easily visualized in the R-R interval data plot, thereby allowing the physician to alter therapy sufficiently to control such potentially damaging rises in heart rate.

Figure 11:
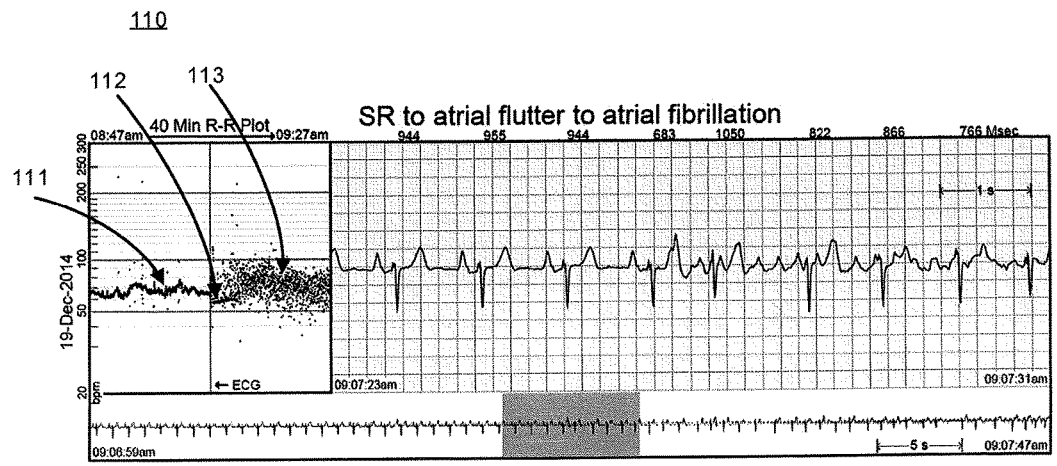
FIG. 11 is a diagram showing, by way of example, a diagnostic composite plot for facilitating the diagnosis of SR transitioning into AFL transitioning into AF.

FIG. 11 is a diagram showing, by way of example, a diagnostic composite plot 110 for facilitating the diagnosis of SR transitioning into AFL transitioning into AF. In a far field view 53 of R-R interval data, SR manifests as an uneven main heart rate line with a fluctuating height 111. At the onset of AFL, the main heart rate line breaks away at a lower heart rate than the SR main heart rate line 112. The episode of AFL further evolves into AF as characterized by a dispersed cloud of irregular heartbeats without concentrated heart rate lines 113. This view provides critical information to the physician managing AF patients in that, at a glance, the view provides data that tells the physician that the patient's AF may be the consequence of AFL. Such knowledge may alter both drug and procedure therapies, like catheter ablation details of intervention.

Figure 12:
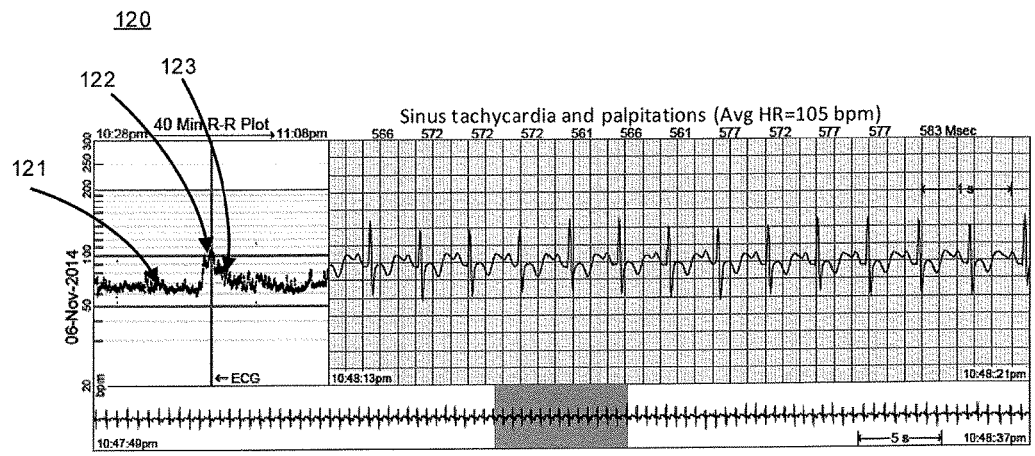
FIG. 12 is a diagram showing, by way of example, a diagnostic composite plot for facilitating the diagnosis of sinus tachycardia and palpitations that occurred during exercise accompanied by a jump in heart rate.

FIG. 12 is a diagram showing, by way of example, a diagnostic composite plot 120 for facilitating the diagnosis of sinus tachycardia and palpitations that occurred during exercise accompanied by a jump in heart rate. In a far field view 50 of R-R interval data, sinus tachycardia is indicated by the presence of a baseline heart rate of about 60 bpm 121 that spikes up to around 100 bpm 122 and gradually slopes down with a wide tail 123, reflecting a sharp rise of heart rates followed by a gradual decline. The associated ECG data in the near field and intermediate field views (not shown) can confirm the rhythm as sinus rhythm and a normal response to exercise. This rhythm, although superficially obvious, was associated with symptoms of palpitations and demonstrates a sensitivity to heart rate fluctuations, rather than a sensitivity to an arrhythmia. This common problem is often dismissed as merely sinus tachycardia, rather than recognizing the context of a changing rate that generated the patient's complaint, a problem, visible only in the R-R interval data plot.

Figure 13:
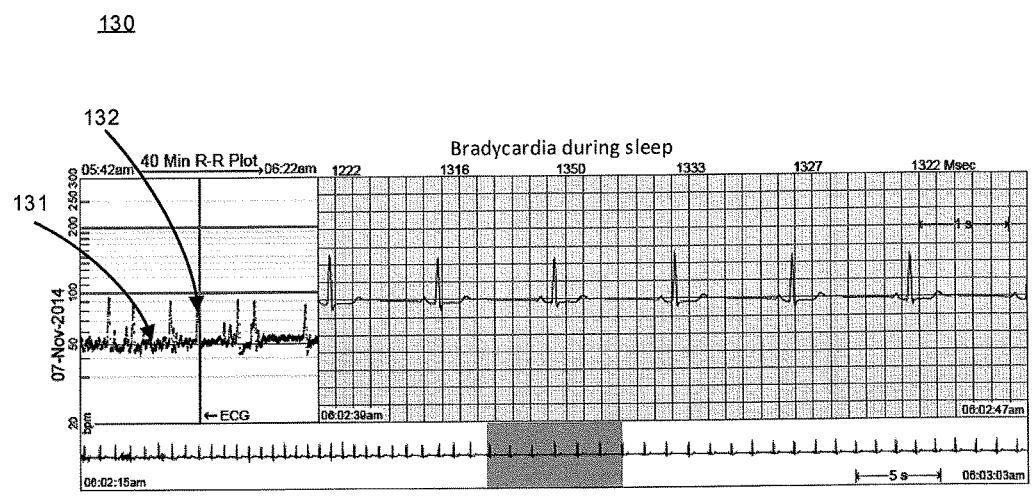
FIG. 13 is a diagram showing, by way of example, a diagnostic composite plot for facilitating the diagnosis of bradycardia.

FIG. 13 is a diagram showing, by way of example, a diagnostic composite plot 90 for facilitating the diagnosis of bradycardia during sleep and a R-R interval pattern characteristic of sleep. Bradycardia refers to a resting heart rate of under 60 bpm. Bradycardia during sleep is often tempered with occasional spikes of rapid heart rate, which can be a secondary compensatory response to dreaming, snoring or sleep apnea. In a far field view 50 of R-R interval data, bradycardia manifests as the presence of a base line heart rate in the range of about 50 bpm 131, coupled with multiple spikes of dots 132 representing intermittent episodes of elevated heart rate. Such elevations in heart rate during a pre-dominantly slower rate may be signs of a cardio-respiratory disorder. Still other applications of the diagnostic composite plot 80 are possible.

The diagnostic composite plots are a tool used by physicians as part of a continuum of cardiac care provisioning that begins with ECG monitoring, continues through diagnostic overread and finally, if medically appropriate, concludes with cardiac rhythm disorder treatment. Each of these steps involve different physical components that collaboratively allow physicians to acquire and visualize R-R interval and ECG data in a way that accurately depicts heart rate variability over time. FIG. 14 is a block diagram showing a system 140 for facilitating diagnosis of cardiac rhythm disorders with the aid of a digital computer 150 in accordance with one embodiment. Each diagnostic composite plot 151 is based on ECG data 166 that has either been recorded by a conventional electrocardiograph (not shown) or retrieved or obtained from some other type of ECG monitoring and recording device. Following completion of the ECG monitoring, the ECG data is assembled into a diagnostic composite plot 151, which can be used by a physician to diagnosis and, if required, treat a cardiac rhythm disorder, or for other health care or related purposes.

Each diagnostic composite plot 151 is based on ECG data 166 that has been recorded over a period of observation, which can be for just a short term, such as during a clinic appointment, or over an extended time frame of months. ECG recordation and, in some cases, physiological monitoring can be provided through various types of ECG-capable monitoring ensembles, including a standardized 12-lead ECG setup (not shown), such as used for clinical ECG monitoring, a portable Holter-type ECG recorder for traditional ambulatory ECG monitoring (also not shown), or a wearable ambulatory ECG monitor.

One form of ambulatory ECG monitor 142 particularly suited to monitoring and recording ECG and physiological data employs an electrode patch 143 and a removable reusable (or single use) monitor recorder 144, such as described in commonly-assigned U.S. patent application Ser. No. 14/997,416, cited supra. The electrode patch 143 and monitor recorder 144 are synergistically optimized to capture electrical signals from the propagation of low amplitude, relatively low frequency content cardiac action potentials, particularly the P-waves generated during atrial activation. The ECG monitor 142 sits centrally (in the midline) on the patient's chest along the sternum 169 oriented top-to-bottom. The ECG monitor 142 interfaces to a pair of cutaneous electrodes (not shown) on the electrode patch 143 that are adhered to the patient's skin along the sternal midline (or immediately to either side of the sternum 169). The ECG monitor 142 has a unique narrow "hourglass"-like shape that significantly improves the ability of the monitor to be comfortably worn by the patient 141 for an extended period of time and to cutaneously sense cardiac electric signals, particularly the P-wave (or atrial activity) and, to a lesser extent, the QRS interval signals in the ECG waveforms indicating ventricular activity.

The electrode patch 143 itself is shaped to conform to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends. To counter dislodgment due to tensile and torsional forces, a strain relief is defined in the electrode patch's flexible circuit using cutouts partially extending transversely from each opposite side of the flexible circuit and continuing longitudinally towards each other to define in 'S'-shaped pattern. In a further embodiment, the electrode patch 143 is made from a type of stretchable spunlace fabric. To counter patient bending motions and prevent disadhesion of the electrode patch 143, the outward-facing aspect of the backing, to which a (non-stretchable) flexible circuit is fixedly attached, stretches at a different rate than the backing's skin-facing aspect, where a skin adhesive removably affixes the electrode patch 143 to the skin. Each of these components are distinctive and allow for comfortable and extended wear, especially by women, where breast mobility would otherwise interfere with ECG monitor use and comfort. Still other forms of ECG monitoring and recording assembles are possible.

When operated standalone, the monitor recorder 142 senses and records the patient's ECG data 166 and physiological data (not shown) into a memory onboard the monitor recorder 144. The recorded data can be downloaded using a download station 145, which could be a dedicated download station 145 that permits the retrieval of stored ECG data 166 and physiological data, if applicable, execution of diagnostics on or programming of the monitor recorder 144, or performance of other functions. To facilitate physical connection with the download station 145, the monitor recorder 144 has a set of electrical contacts (not shown) that enable the monitor recorder 144 to physically interface to a set of terminals 148. In turn, the download station 145 can be operated through user controls 149 to execute a communications or data download program 146 ("Download") or similar program that interacts with the monitor recorder 144 via the physical interface to retrieve the stored ECG data 166. The download station 145 could alternatively be a server, personal computer, tablet or handheld computer, smart mobile device, or purpose-built device designed specific to the task of interfacing with a monitor recorder 144. Still other forms of download station 145 are possible. In a further embodiment, the ECG data 166 from the monitor recorder 144 can be offloaded wirelessly.

The ECG data 166 can be retrieved from the download station 145 using a control program 157 ("Ctl") or analogous application executing on a personal digital computer 156 or other connectable computing device, via a hard wired link 158, wireless link (not shown), or by physical transfer of storage media (not shown). The personal digital computer 156 may also execute middleware (not shown) that converts the ECG data 166 into a format suitable for use by a third-party post-monitoring analysis program. The personal digital computer 156 stores the ECG data 166 along with each patient's electronic medical records (EMRs) 165 in the secure database 64, as further discussed infra. In a further embodiment, the download station 145 is able to directly interface with other devices over a computer communications network 155, which could be a combination of local area and wide area networks, including the Internet or another telecommunications network, over wired or wireless connections.

A client-server model can be employed for ECG data 166 analysis. In this model, a server 62 executes a patient management program 160 ("Mgt") or similar application that accesses the retrieved ECG data 166 and other information in the secure database 164 cataloged with each patient's EMRs 165. The patients' EMRs can be supplemented with other information (not shown), such as medical history, testing results, and so forth, which can be factored into automated diagnosis and treatment. The patient management program 160, or other trusted application, also maintains and safeguards the secure database 164 to limit access to patient EMRs 165 to only authorized parties for appropriate medical or other uses, such as mandated by state or federal law, such as under the Health Insurance Portability and Accountability Act (HIPAA) or per the European Union's Data Protection Directive. Other schemes and safeguards to protect and maintain the integrity of patient EMRs 165 are possible.

In a further embodiment, the wearable monitor 142 can interoperate wirelessly with other wearable or implantable physiology monitors and activity sensors 152, such as activity trackers worn on the wrist or body, and with mobile devices 153, including smart watches and smartphones. Wearable or implantable physiology monitors and activity sensors 152 encompass a wide range of wirelessly interconnectable devices that measure or monitor a patient's physiological data, such as heart rate, temperature, blood pressure, respiratory rate, blood pressure, blood sugar (with or without an appropriate subcutaneous probe), oxygen saturation, minute ventilation, and so on; physical states, such as movement, sleep, footsteps, and the like; and performance, including calories burned or estimated blood glucose level. Frequently, wearable and implantable physiology monitors and activity sensors 152 are capable of wirelessly interfacing with mobile devices 153, particularly smart mobile devices, including so-called "smartphones" and "smart watches," as well as with personal computers and tablet or handheld computers, to download monitoring data either in real-time or in batches through an application ("App") or similar program.

Based on the ECG data 166, physicians can rely on the data as medically certifiable and are able to directly proceed with diagnosing cardiac rhythm disorders and determining the appropriate course of treatment for the patient 141, including undertaking further medical interventions as appropriate. The ECG data 166 can be retrieved by a digital computer 150 over the network 155. A diagnostic composite plot 151 that includes multiple temporal points of reference and a plot of R-R interval data is then constructed based on the ECG data 166, as discussed in detail supra with reference to FIG. 3, and displayed or, alternatively, printed, for use by a physician.

In a further embodiment, the server 159 executes a patient diagnosis program 161 ("Dx") or similar application that can evaluate the ECG data 166 to form a diagnosis of a cardiac rhythm disorder. The patient diagnosis program 161 compares and evaluates the ECG data 166 to a set of medical diagnostic criteria 167, from which a diagnostic overread 162 ("diagnosis") is generated. Each diagnostic overread 162 can include one or more diagnostic findings 168 that can be rated by degree of severity, such as with the automated diagnosis of atrial fibrillation. If at least one of the diagnostic findings 168 for a patient exceed a threshold level of tolerance, which may be tailored to a specific client, disease or medical condition group, or applied to a general patient population, in a still further embodiment, therapeutic treatment ("Therapy") to address diagnosed disorder findings can be generated and, optionally, programmed into a cardiac rhythm therapy delivery device, such as an IMD (not shown), including a pacemaker, implantable cardioverter defibrillator (ICD), or similar devices.

Figure 15:
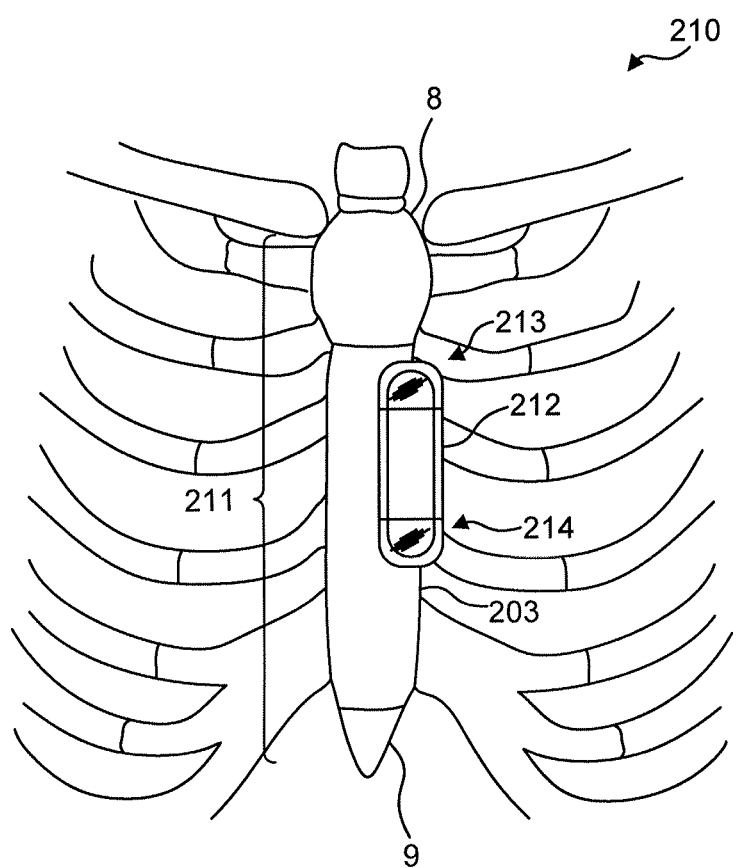
FIG. 15 is a diagram showing, by way of example, a subcutaneous P-wave centric insertable cardiac monitor (ICM) for long term electrocardiographic monitoring in accordance with one embodiment.

In a further embodiment, the ECG data 166 can be recorded using a subcutaneous insertable cardiac monitor. Long-term electrocardiographic and physiological monitoring over a period lasting up to several years in duration can be provided through a continuously-recording subcutaneous insertable cardiac monitor (ICM), such as one described in commonly-owned U.S. patent application Ser. No. 15/832,385, filed Dec. 5, 2017, pending, the disclosure of which is incorporated by reference. FIG. 15 is a diagram showing, by way of example, a subcutaneous P-wave centric ICM 212 for long term electrocardiographic monitoring in accordance with one embodiment. The ICM 212 is implanted in the parasternal region 211 of a patient 210. The sensing circuitry and components, compression algorithms, and the physical layout of the electrodes are specifically optimized to capture electrical signals from the propagation of low amplitude, relatively low frequency content cardiac action potentials, particularly the P-waves generated during atrial activation. The position and placement of the ICM 212 coupled to engineering considerations that optimize the ICM's sensing circuitry, discussed infra, aid in demonstrating the P-wave clearly.

Implantation of a P-wave centric ICM 212 in the proper subcutaneous site facilitates the recording of high quality ECG data with a good delineation of the P-wave. In general, the ICM 212 is intended to be implanted anteriorly and be positioned axially and slightly to either the right or left of the sternal midline in the parasternal region 211 of the chest, or if sufficient subcutaneous fat exists, directly over the sternum. Optimally, the ICM 212 is implanted in a location left parasternally to bridge the left atrial appendage. However, either location to the right or left of the sternal midline is acceptable; placement of the device, if possible, should bridge the vertical height of the heart, which lies underneath the sternum 203, thereby placing the ICM 212 in close proximity to the anterior right atrium and the left atrial appendage that lie immediately beneath.

The ICM 212 is shaped to fit comfortably within the body under the skin and to conform to the contours of the patient's parasternal region 211 when implanted immediately to either side of the sternum 203, but could be implanted in other locations of the body. In most adults, the proximal end 213 of the ICM 212 is generally positioned below the manubrium 8 but, depending upon patient's vertical build, the ICM 212 may actually straddle the region over the manubrium 8. The distal end 214 of the ICM 212 generally extends towards the xiphoid process 9 and lower sternum but, depending upon the patient's build, may actually straddle the region over or under the xiphoid process 9, lower sternum and upper abdomen.

Although internal tissues, body structures, and tissue boundaries can adversely affect the current strength and signal fidelity of all body surface potentials, subsurface low amplitude cardiac action potentials, particularly P-wave signals with a normative amplitude of less than 0.25 millivolts (mV) and a normative duration of less than 120 milliseconds (ms), are most apt to be negatively impacted by these factors. The atria, which generate the P wave, are mostly located posteriorly within the thoracic cavity (with the exception of the anterior right atrium, right atrial appendage and left atrial appendage). The majority of the left atrium constitutes the portion of the heart furthest away from the surface of the skin on the chest and harbors the atrial tissue most likely to be the source of serious arrhythmias, like atrial fibrillation. Conversely, the ventricles, which generate larger amplitude signals, are located anteriorly as in the case of the anterior right ventricle and most of the anterior left ventricle situated relatively close to the skin surface of the central and left anterior chest. These factors, together with larger size and more powerful impulse generation from the ventricles, contribute to the relatively larger amplitudes of ventricular waveforms.

Nevertheless, both the P-wave and the R-wave are required for the physician to make a proper rhythm diagnosis from the dozens of arrhythmias that can occur. Yet, the quality of P-waves is more susceptible to weakening from distance and the intervening tissues and structures and from signal attenuation and signal processing than the high voltage waveforms associated with ventricular activation. The added value of avoiding further signal attenuation resulting from dermal impedance makes a subcutaneous P-wave centric ICM even more likely to match, or even outperform dermal ambulatory monitors designed to analogous engineering considerations and using similar sensing circuitry and components, compression algorithms, and physical layout of electrodes, such as described in U.S. Pat. No. 9,545,204, issued January 217, 20217 to Bishay et al.; U.S. Pat. No. 9,730,593, issued Aug. 15, 20217 to Felix et al.; U.S. Pat. No. 9,700,227, issued Jul. 11, 20217 to Bishay et al.; U.S. Pat. No. 97,217,433, issued Aug. 1, 20217 to Felix et al.; and U.S. Pat. No. 9,615,763, issued Apr. 11, 20217 to Felix et al., the disclosures of which are incorporated by reference.

The ICM 212 can be implanted in the patient's chest using, for instance, a minimally invasive subcutaneous implantation instrument or other suitable surgical implement. The ICM 212 is positioned slightly to the right or left of midline, covering the center third of the chest, roughly between the second and sixth ribs, approximately spanning between the level of the manubrium 8 and the level of the xiphoid process 9 on the inferior border of the sternum 203, depending upon the vertical build of the patient 210.

During monitoring, the amplitude and strength of action potentials sensed by an ECG devices, including dermal ECG monitors and ICMs, can be affected to varying degrees by cardiac, cellular, extracellular, vector of current flow, and physical factors, like obesity, dermatitis, lung disease, large breasts, and high impedance skin, as can occur in dark-skinned individuals. Performing ECG sensing subcutaneously in the parasternal region 211 significantly improves the ability of the ICM 212 to counter some of the effects of these factors, particularly high skin impedance and impedance from subcutaneous fat. Thus, the ICM 212 exhibits superior performance when compared to conventional dermal ECG monitors to existing implantable loop recorders, ICMs, and other forms of implantable monitoring devices by virtue of its engineering and proven P-wave documentation above the skin, as discussed in W. M. Smith et al., "Comparison of diagnostic value using a small, single channel, P-wave centric sternal ECG monitoring patch with a standard 3-lead Holter system over 24 hours," Am. Heart J., March 20217; 2185:67-73, the disclosure of which is incorporated by reference.

Moreover, the sternal midline implantation location in the parasternal region 211 allows the ICM's electrodes to record an ECG of optimal signal quality from a location immediately above the strongest signal-generating aspects of the atrial. Signal quality is improved further in part because cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the atrioventricular (AV) node. On the proximal end 213, the ECG electrodes of the ICM 212 are subcutaneously positioned with the upper or superior pole (ECG electrode) slightly to the right or left of the sternal midline in the region of the manubrium 8 and, on the distal end 214, the lower or inferior pole (ECG electrode) is similarly situated slightly to the right or left of the sternal midline in the region of the xiphoid process 9 and lower sternum 203. The ECG electrodes of the ICM 212 are placed primarily in a north-to-south orientation along the sternum 203 that corresponds to the north-to-south waveform vector exhibited during atrial activation. This orientation corresponds to the aVF lead used in a conventional 12-lead ECG that is used to sense positive or upright P-waves. In addition, the electrode spacing and the electrodes' shapes and surface areas mimic the electrodes used in the ICM's dermal cousin, designed as part of the optimal P-wave sensing electrode configuration, such as provided with the dermal ambulatory monitors cited supra.

Figure 16:
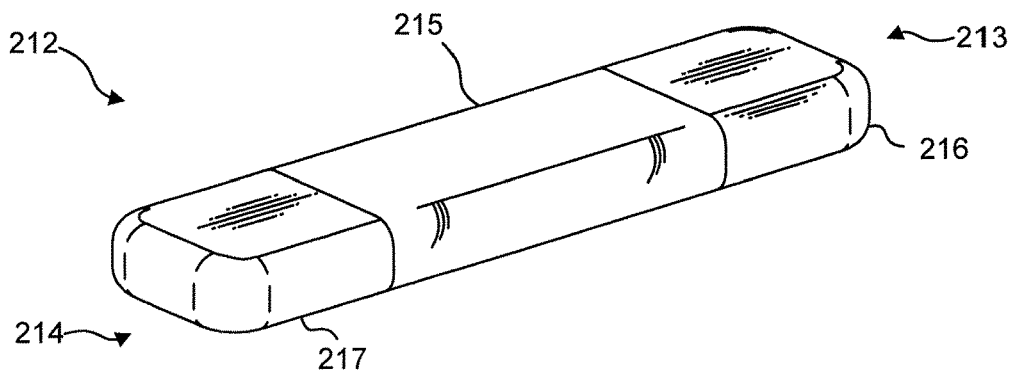
FIGS. 16 and 17 are respectively top and bottom perspective views showing the ICM of FIG. 15.
Figure 17:
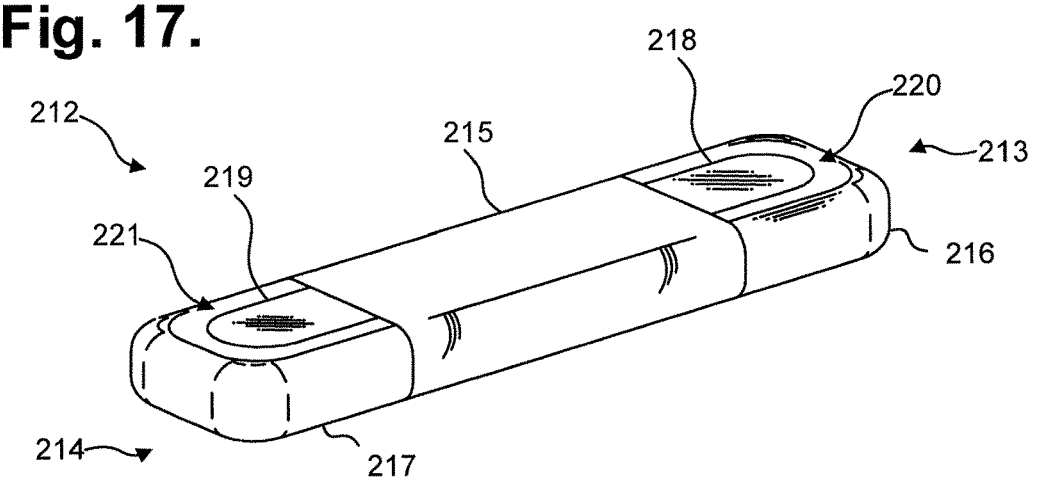

Despite the challenges faced in capturing low amplitude cardiac action potentials, the ICM 212 is able to operate effectively using only two electrodes that are strategically sized and placed in locations ideally suited to high fidelity P-wave signal acquisition. This approach has been shown to clinically outperform more typical multi-lead monitors because of the improved P-wave clarity, as discussed in W. M. Smith et al., cited supra. FIGS. 16 and 17 are respectively top and bottom perspective views showing the ICM 212 of FIG. 1. Physically, the ICM 212 is constructed with a hermetically sealed implantable housing 215 with at least one ECG electrode forming a superior pole on the proximal end 213 and at least one ECG electrode forming an inferior pole on the distal end 214.

When implanted, the housing 215 is oriented most cephalad. The housing 215 is constructed of titanium, stainless steel or other biocompatible material. The housing 215 contains the sensing, recordation and interfacing circuitry of the ICM 212, plus a long life battery. A wireless antenna is integrated into or within the housing 215 and can be positioned to wrap around the housing's internal periphery or location suited to signal reception. Other wireless antenna placement or integrations are possible.

Physically, the ICM 212 has four ECG electrodes 216, 217, 218, 219. There could also be additional ECG electrodes, as discussed infra. The ECG electrodes include two ventral (or dorsal) ECG electrodes 218, 219 and two wraparound ECG electrodes 216, 217. One ventral ECG electrode 218 is formed on the proximal end 213 and one ventral ECG electrode 219 is formed on the distal end 214. One wraparound ECG electrode 216 is formed circumferentially about the proximal end 213 and one wraparound ECG electrode 217 is formed circumferentially about the distal end 214. Each wraparound ECG electrode 216, 217 is electrically insulated from its respective ventral ECG electrode 218, 219 by a periphery 220, 221.

The four ECG electrodes 216, 217, 218, 219 are programmatically controlled by a microcontroller through onboard firmware programming to enable a physician to choose from several different electrode configurations that vary the electrode surface areas, shapes, and inter-electrode spacing. The sensing circuitry can be programmed, either pre-implant or in situ, to use different combinations of the available ECG electrodes (and thereby changing electrode surface areas, shapes, and inter-electrode spacing), including pairing the two ventral ECG electrodes 216, 217, the two wraparound ECG electrodes 218, 219, or one ventral ECG electrode 216, 217 with one wraparound ECG electrode 218, 219 located on the opposite end of the housing 215. In addition, the periphery 220, 221 can be programmatically controlled to logically combine the wraparound ECG electrode 216, 217 on one end of the ICM 212 with its corresponding ventral ECG electrode 218, 219 to form a single virtual ECG electrode with larger surface area and shape. (Although electronically possible, the two ECG electrodes that are only on one end of the ICM 212, for instance, wraparound ECG electrode 216 and ventral ECG electrode 218, could be paired; however, the minimal inter-electrode spacing would likely yield a signal of poor fidelity in most situations.)

In a further embodiment, the housing 215 and contained circuitry can be provided as a standalone ICM core assembly to which a pair of compatible ECG electrodes can be operatively coupled to form a full implantable ICM device.

Figure 18:
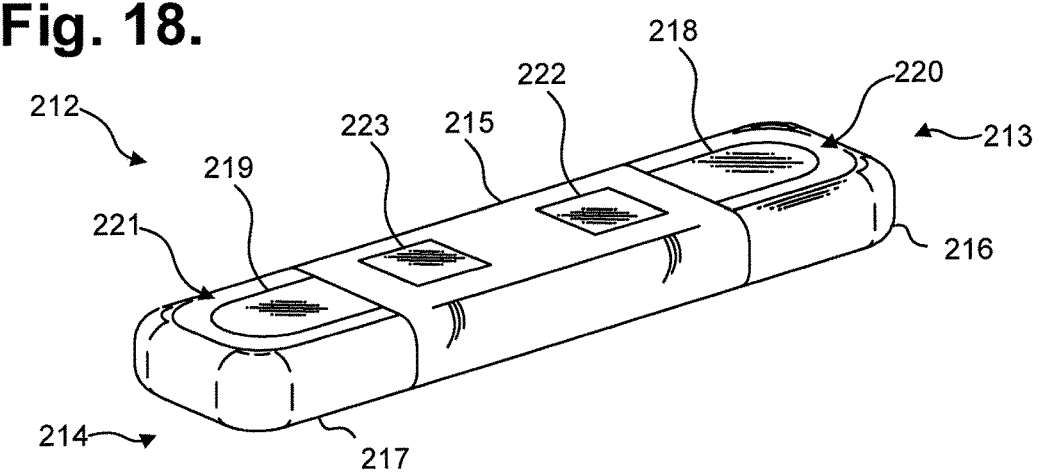
FIG. 18 is a bottom perspective view showing the ICM of FIG. 15 in accordance with a further embodiment.

Other ECG electrode configurations are possible. For instance, additional ECG electrodes can be provided to increase the number of possible electrode configurations, all of which are to ensure better P-wave resolution. FIG. 18 is a bottom perspective view showing the ICM 212 of FIG. 15 in accordance with a further embodiment. An additional pair of ventral ECG electrodes 222, 223 are included on the housing's ventral surface. These ventral ECG electrodes 222, 223 are spaced closer together than the ventral ECG electrodes 218, 219 on the ends of the housing 215 and a physician can thus choose to pair the two inner ventral ECG electrodes 222, 223 by themselves to allow for minimal electrode-to-electrode spacing, or with the other ECG electrodes 216, 217, 218, 219 to vary electrode surface areas, shapes, and inter-electrode spacing even further to explore optimal configurations to acquire the P-wave.

Figure 19:
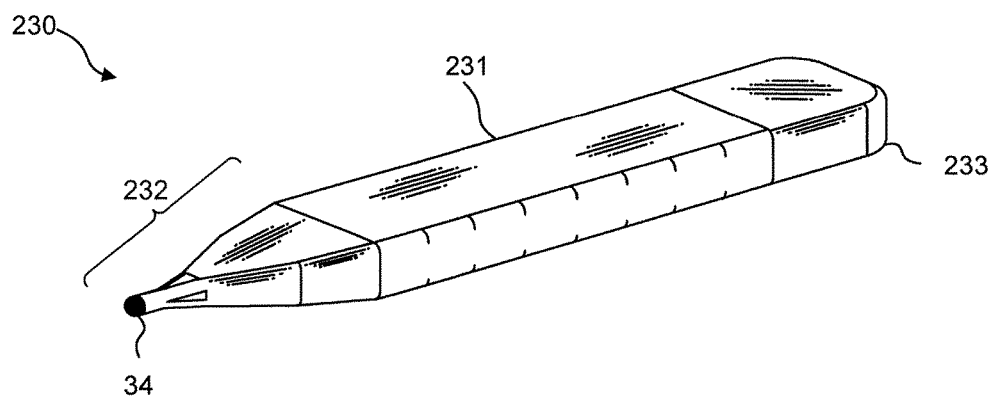
FIGS. 19 and 20 are respectively top and bottom perspective views showing an ICM in accordance with a still further embodiment.
Figure 20:
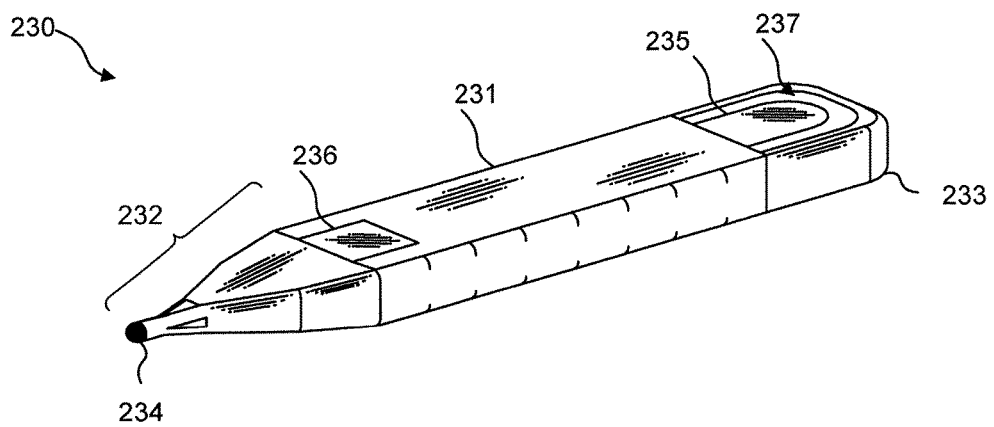

Other housing configurations of the ICM are possible. For instance, the housing of the ICM can be structured to enhance long term comfort and fitment, and to accommodate a larger long life battery or more circuitry or features, including physiologic sensors, to provide additional functionality. FIGS. 19 and 20 are respectively top and bottom perspective views showing an ICM 230 in accordance with a still further embodiment. The ICM 230 has a housing 31 with a tapered extension 32 that is terminated on the distal end with an electrode 34. On a proximal end, the housing 31 includes a pair of ECG electrodes electrically insulated by a periphery 37 that include a ventral ECG electrode 33 and a wraparound ECG electrode 34. In addition, a ventral ECG electrode 36 is oriented on the housing's distal end before the tapered extension 32. Still other housing structures and electrode configurations are possible.

In general, the basic electrode layout is sufficient to sense cardiac action potentials in a wide range of patients. Differences in thoracic tissue density and skeletal structure from patient to patient, though, can affect the ability of the sensing electrodes to efficaciously capture action potential signals, yet the degree to which signal acquisition is affected may not be apparent until after an ICM has been implanted and deployed, when the impacts of the patient's physical constitution and his patterns of mobility and physical movement on ICM monitoring can be fully assessed.

Figure 21:
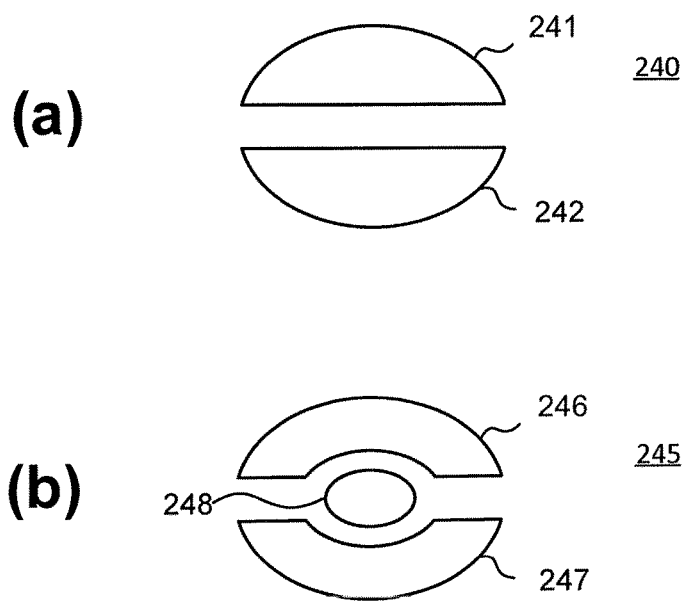
FIG. 21 is a plan view showing further electrode configurations.

In further embodiments, the electrodes can be configured post-implant to allow the ICM to better adapt to a particular patient's physiology. For instance, electrode configurations having more than two sensing electrodes are possible. FIG. 21 is a plan view showing further electrode configurations. Referring first to FIG. 21(a), a single disc ECG electrode 40 could be bifurcated to form a pair of half-circle ECG electrodes 241, 242 that could be programmatically selected or combined to accommodate a particular patients ECG signal characteristics post-ICM implant. Referring next to FIG. 21(b), a single disc ECG electrode 245 could be divided into three sections, a pair of crescent-shaped ECG electrodes 246, 247 surrounding a central semicircular ECG electrode 48 that could similarly be programmatically selected or combined. Still other ECG electrode configurations are possible.

Figure 22:
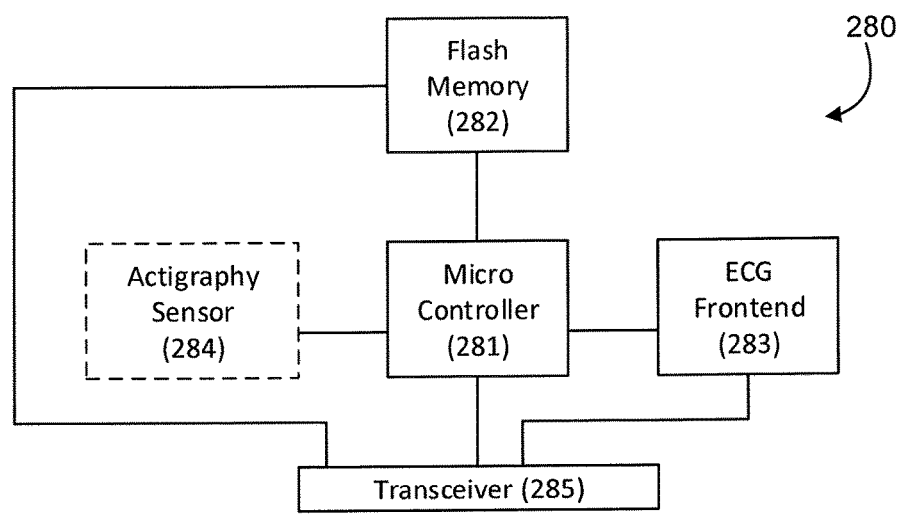
FIG. 22 is a functional block diagram showing the P-wave focused component architecture of the circuitry of the ICM of FIG. 15.

ECG monitoring and other functions performed by the ICM 212 are provided through a micro controlled architecture. FIG. 22 is a functional block diagram showing the P-wave focused component architecture of the circuitry 280 of the ICM 212 of FIG. 15. The circuitry 280 is powered through the long life battery 21 provided in the housing 215. Operation of the circuitry 280 of the ICM 212 is managed by a microcontroller 281, such as the EFM32 Tiny Gecko 32-bit microcontroller, manufactured by Silicon Laboratories Inc., Austin, Tex. The microcontroller 281 has flexible energy management modes and includes a direct memory access controller and built-in analog-to-digital and digital-to-analog converters (ADC and DAC, respectively). The microcontroller 281 also includes a program memory unit containing internal flash memory (not shown) that is readable, writeable, and externally programmable.

The microcontroller 281 operates under modular micro program control as specified in firmware stored in the internal flash memory. The microcontroller 281 draws power from the battery provided in the housing 215 and connects to the ECG front end circuit 283. The front end circuit 283 measures raw subcutaneous electrical signals using a driven reference signal that eliminates common mode noise, as further described infra.

The circuitry 280 of the ICM 212 also includes a flash memory 82 external to the microcontroller 281, which the microcontroller 281 uses for continuously storing samples of ECG monitoring signal data and other physiology, such as respiratory rate, blood oxygen saturation level ($SpO_2$), blood pressure, temperature sensor, and physical activity, and device and related information. The flash memory 82 also draws power from the battery provided in the housing 215. Data is stored in a serial flash memory circuit, which supports read, erase and program operations over a communications bus. The flash memory 82 enables the microcontroller 281 to store digitized ECG data. The communications bus further enables the flash memory 82 to be directly accessed wirelessly through a transceiver 285 coupled to an antenna 217 built into (or provided with) the housing 215. The transceiver 285 can be used for wirelessly interfacing over Bluetooth or other types of wireless technologies for exchanging data over a short distance with a paired mobile device, including smartphones and smart watches, that are designed to communicate over a public communications infrastructure, such as a cellular communications network, and, in a further embodiment, other wearable (or implantable) physiology monitors, such as activity trackers worn on the wrist or body. Other types of device pairings are possible, including with a desktop computer or purpose-built bedside monitor. The transceiver 285 can be used to offload stored ECG monitoring data and other physiology data and information, such as by wirelessly transmitting the samples of ECG signals stored in the flash memory 82 to the download station and any other physiological data to the download station 145, and for device firmware reprogramming. In a further embodiment, the flash memory 82 can be accessed through an inductive coupling (not shown), with the accessed samples of the ECG signals being provided to the download station 145.

The microcontroller 281 includes functionality that enables the acquisition of samples of analog ECG signals, which are converted into a digital representation. In one mode, the microcontroller 281 implements a loop recorder feature that will acquire, sample, digitize, signal process, and store digitized ECG data into available storage locations in the flash memory 82 until all memory storage locations are filled, after which existing stored digitized ECG data will either be overwritten through a sliding window protocol, albeit at the cost of potentially losing the stored data that was overwritten, if not previously downloaded, or transmitted wirelessly to an external receiver, such as the download station 145, to unburden the flash memory. In another mode, the stored digitized ECG data can be maintained permanently until downloaded or erased to restore memory capacity. Data download or erasure can also occur before all storage locations are filled, which would free up memory space sooner, albeit at the cost of possibly interrupting monitoring while downloading or erasure is performed. Still other modes of data storage and capacity recovery are possible.

The circuitry 280 of the ICM 212 can include functionality to programmatically select pairings of sensing electrodes when the ICM 212 is furnished with three or more electrodes. In a further embodiment, multiple sensing electrodes could be provided on the ICM 212 to provide a physician the option of fine-tuning the sensing dipole (or tripole or multipole) in situ by parking active electrodes and designating any remaining electrodes inert. The pairing selection can be made remotely through an inductive coupling or by the transceiver 285 via, for instance, a paired mobile device. Thus, the sensing electrode configuration, including number of electrodes, electrode-to-electrode spacing, and electrode size, shape, surface area, and placement, can be modified at any time during the implantation of the ICM 212.

In a further embodiment, the circuitry 280 of the ICM 212 can include an actigraphy sensor 84 implemented as a 3-axis accelerometer. The accelerometer may be configured to generate interrupt signals to the microcontroller 281 by independent initial wake up and free fall events, as well as by device position. In addition, the actigraphy provided by the accelerometer can be used during post-monitoring analysis to correct the orientation of the ICM 212 if, for instance, the ICM 212 has been inadvertently implanted upside down, that is, with the ICM's housing oriented caudally, as well as for other event occurrence analyses.

In a still further embodiment, the circuitry 280 of the ICM 212 can include one or more physiology sensors. For instance, a physiology sensor can be provided as part of the circuitry 280 of the ICM 212, or can be provided on the electrode assembly 14 with communication with the microcontroller 281 provided through a circuit trace. The physiology sensor can include an $SpO_2$ sensor, blood pressure sensor, temperature sensor, respiratory rate sensor, glucose sensor, airflow sensor, volumetric pressure sensing, or other types of sensor or telemetric input sources.

In a yet further embodiment, firmware with programming instructions, including machine learning and other forms of artificial intelligence-originated instructions, can be downloaded into the microcontroller's internal flash memory. The firmware can include heuristics to signal patient and physician with alerts over health conditions or arrhythmias of selected medical concern, such as where a heart pattern particular to the patient is identified and the ICM 212 is thereby reprogrammed to watch for a reoccurrence of that pattern, after which an alert will be generated and sent to the physician (or other caregiver) through the transceiver 285 via, for instance, a paired mobile device. Similarly, the firmware can include heuristics that can be downloaded to the ICM 212 to actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver) through the transceiver 285. For instance, an alert that includes a compressed ECG digitized sample can also be wirelessly transmitted by the ICM 212 upon the triggering of a preset condition, such as an abnormally low heart rate in excess of 170 beats per minute (bpm), an abnormally low heart rate falling below 30 bpm, or AF detected by onboard analysis of RR interval variability by the microcontroller 61. Finally, a similar methodology of creating firmware programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Finally, in a still further embodiment, the circuitry 280 of the ICM 212 can accommodate patient-interfaceable components, including an external tactile feedback device (not shown) that wirelessly interfaces to the ICM 212 through the transceiver 285. A patient 210 can press the external tactile feedback device to mark events, such as a syncope episode, or to perform other functions. The circuitry 280 can also accommodate triggering an external buzzer 267, such as a speaker, magnetic resonator or piezoelectric buzzer, implemented as part of the external tactile feedback device or as a separate wirelessly-interfaceable component. The buzzer 67 can be used by the microcontroller 281 to indirectly output feedback to a patient 210, such as a low battery or other error condition or warning. Still other components, provided as either part of the circuitry 280 of the ICM 212 or as external wirelessly-interfaceable devices, are possible.

In a further embodiment, the ECG front end circuit 283 of the ICM 212 measures raw subcutaneous electrical signals using a driven reference signal, such as described in U.S. Pat. Nos. 9,700,227, 9,7217,433, and 9,615,763, cited supra. The driven reference signal effectively reduces common mode noise, power supply noise and system noise, which is critical to preserving the characteristics of low amplitude cardiac action potentials, especially the P wave signals originating from the atria.

The ECG front end circuit 283 is organized into a passive input filter stage, a unity gain voltage follower stage, a passive high pass filtering stage, a voltage amplification and active filtering stage, and an anti-aliasing passive filter stage, plus a reference generator. The passive input filter stage passively shifts the frequency response poles downward to counter the high electrode impedance from the patient on the signal lead and reference lead, which reduces high frequency noise. The unity gain voltage follower stage allows the circuit to accommodate a very high input impedance, so as not to disrupt the subcutaneous potentials or the filtering effect of the previous stage. The passive high pass filtering stage includes a high pass filter that removes baseline wander and any offset generated from the previous stage. As necessary, the voltage amplification and active filtering stage amplifies or de-amplifies (or allows to pass-through) the voltage of the input signal, while applying a low pass filter. The anti-aliasing passive filter stage provides an anti-aliasing low pass filter. The reference generator drives a driven reference signal containing power supply noise and system noise to the reference lead and is connected directly to the patient, thereby avoiding the thermal noise of the protection resistor that is included as part of the protection circuit.

While the invention has been particularly shown and described as referenced to the embodiments thereof, those skilled in the art will understand that the foregoing and other changes in form and detail may be made therein without departing from the spirit and scope.

What is claimed is:

1. A system for facilitating a cardiac rhythm disorder diagnosis based on subcutaneous cardiac monitoring data, comprising:
   a subcutaneous insertable cardiac monitor, comprising:
      an implantable housing for implantation within a living body, the implantable housing comprised of a biocompatible material;
      at least one pair of electrocardiographic (ECG) sensing electrodes provided on a ventral surface and on opposite ends of the implantable housing operatively placed to facilitate sensing in closest proximity to low amplitude, low frequency content cardiac action potentials that are generated during atrial activation; and
      electronic circuitry provided within the housing assembly comprising a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and non-volatile memory electrically interfaced with the microcontroller and operable to continuously store samples of the ECG signals; and
   a download station adapted to retrieve the stored samples of the ECG signals from the subcutaneous insertable cardiac monitor as ECG data;
   a computer comprising a processor and memory within which code for execution by the processor is stored, the processor configured to:
      receive the ECG data retrieved by the download station;
      identify a set of R-wave peaks within the ECG data;
      construct an R-R interval plot, comprising:
         determine a difference between recording times of successive pairs of the R-wave peaks in the set and determine a heart rate associated with each difference;
         plot the pairs of the R-wave peaks and associated heart rate as the R-R interval plot; and
         accentuate in the R-R interval plot spatial differences in frequently-occurring ranges of the heart rate and de-emphasize the spatial differences in ranges of the heart rate where a deviation from the frequently-occurring ranges exists using a non-linear scale for the heart rate; and
   a display to facilitate diagnosis of a cardiac disorder of the patient based on patterns of the plotted pairs of the R-wave peaks and the associated heart rates in the R-R interval plot.

2. A system in accordance with claim 1, the processor further configured to:
   form a diagnosis based on heart rate variability patterns in the R-R interval plot.

3. A system in accordance with claim 2, the processor further configured to:
   detect atrial fibrillation by identifying a Gaussian-type distribution of heart rate variability in the duration R-R interval plot.

4. A system in accordance with claim 1, wherein the processor is configured to form:

a background information plot with the R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature; and background information layered to or keyed with the R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature.

5. A system in accordance with claim 1, wherein the display displays the R-R interval plot with one or more views of at least a portion of the ECG data as contextual data for the R-R interval plot.

6. A system in accordance with claim 1, wherein each ECG data view comprises one of a near field view providing ECG data corresponding to the data for the R-wave peak pairs at a center of the R-R interval plot and an intermediate field view providing presentation of additional ECG data than the near field view.

7. A system in accordance with claim 1, wherein the set of R-wave peaks is collected over a period of at least 40 minutes.

8. A system in accordance with claim 1, the processor further configured to:
select the set of R-wave peaks by identifying a potential cardiac event within the ECG data and obtaining a portion of the ECG data corresponding to a time during, prior to, and after the potential cardiac event as the set of R-wave peaks.

9. A system in accordance with claim 8, the processor further configured to:
represent the potential cardiac event in the R-R interval plot via a temporal point of reference.

10. A system in accordance with claim 9, wherein the display displays the temporal point of reference in the R-R interval plot in one of a center and another location.

11. A method for facilitating a cardiac rhythm disorder diagnosis based on subcutaneous cardiac monitoring data, comprising:
recording cardiac action potentials of a patient over a set time period using a subcutaneous insertable cardiac monitor, the subcutaneous insertable cardiac monitor comprising an implantable housing for implantation within a living body, the implantable housing comprised of a biocompatible material, the subcutaneous insertable cardiac monitor further comprising at least one pair of electrocardiographic (ECG) sensing electrodes provided on a ventral surface and on opposite ends of the implantable housing operatively placed to facilitate sensing in closest proximity to low amplitude, low frequency content cardiac action potentials that are generated during atrial activation, the subcutaneous insertable cardiac monitor further comprising electronic circuitry provided within the housing assembly, the electronic circuitry comprising a low power microcontroller operable to execute under modular micro program control as specified in firmware, an ECG front end circuit interfaced to the microcontroller and configured to capture the cardiac action potentials sensed by the pair of ECG sensing electrodes which are output as ECG signals, and a non-volatile memory electrically interfaced with the microcontroller and operable to continuously store samples of the ECG signals; and retrieving the stored samples of the ECG signals as ECG data;
identifying a set of R-wave peaks within the ECG data;
constructing an R-R interval plot, comprising:
determining a difference between recording times of successive pairs of the R-wave peaks in the set;
determining a heart rate associated with each difference;
plotting the pairs of the R-wave peaks and associated heart rate as the R-R interval plot; and
accentuating in the R-R interval plot spatial differences in frequently-occurring ranges of the heart rate and de-emphasizing the spatial differences in ranges of the heart rate where a deviation from the frequently-occurring ranges exists using a non-linear scale for the heart rate; and
facilitating diagnosis of a cardiac disorder of the patient based on patterns of the plotted pairs of the R-wave peaks and the associated heart rates in the R-R interval plot.

12. A method in accordance with claim 11, further comprising:
forming a diagnosis based on heart rate variability patterns in the R-R interval plot.

13. A method in accordance with claim 12, further comprising:
detecting atrial fibrillation by identifying a Gaussian-type distribution of heart rate variability in the duration R-R interval plot.

14. A method in accordance with claim 11, further comprising at least one of:
including a background information plot with the R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature; and
layering or keying background information with the R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature.

15. A method in accordance with claim 11, further comprising:
displaying the R-R interval plot with one or more views of at least a portion of the ECG data as contextual data for the R-R interval plot.

16. A method in accordance with claim 11, wherein each ECG data view comprises one of a near field view providing ECG data corresponding to the data for the R-wave peak pairs at a center of the R-R interval plot and an intermediate field view providing presentation of additional ECG data than the near field view.

17. A method in accordance with claim 11, wherein the set of R-wave peaks is collected over a period of at least 40 minutes.

18. A method in accordance with claim 11, further comprising:
selecting the set of R-wave peaks, comprising:
identifying a potential cardiac event within the ECG data; and
obtaining a portion of the ECG data corresponding to a time during, prior to, and after the potential cardiac event as the set of R-wave peaks.

19. A method in accordance with claim 18, further comprising:

representing the potential cardiac event in the R-R interval plot via a temporal point of reference.

20. A method in accordance with claim 19, further comprising:
displaying the temporal point of reference in the R-R interval plot in one of a center and another location.

* * * * *